United States Patent [19]
Freed et al.

[11] 3,976,693
[45] Aug. 24, 1976

[54] BENZOBICYCLOALKANONE OXIMES

[75] Inventors: Meier E. Freed, Paoli; John R. Potoski, Spring City, both of Pa.

[73] Assignee: American Home Products Corporation, New York, N.Y.

[22] Filed: July 17, 1975

[21] Appl. No.: 596,923

Related U.S. Application Data

[60] Continuation-in-part of Ser. No. 421,306, Dec. 3, 1973, abandoned, which is a division of Ser. No. 262,849, June 14, 1972, Pat. No. 3,836,670, which is a continuation-in-part of Ser. No. 200,517, Nov. 19, 1971, abandoned, which is a continuation-in-part of Ser. No. 94,983, Dec. 3, 1970, abandoned.

[52] U.S. Cl. ................. 260/566 A; 260/468 R; 260/468 H; 260/476 C; 260/479 R; 260/570.5 CA; 424/330

[51] Int. Cl.$^2$ ........................................ C07C 131/04
[58] Field of Search ........ 260/566 A, 468 R, 476 C, 260/479 R

[56] References Cited
OTHER PUBLICATIONS

Mitsuhashi et al., Chemical & Pharmaceutical Bull. of Tokoyo vol. 18, pp. 75–87 (1970).

*Primary Examiner*—Gerald A. Schwartz
*Attorney, Agent, or Firm*—Robert Wiser

[57] ABSTRACT

Benzobicycloalkanone oximes which are intermediates for the preparation of benzobicycloalkane amines. The amines exert analgesic and antiinflammatory effects in warm-blooded animals.

8 Claims, No Drawings

BENZOBICYCLOALKANONE OXIMES

CROSS-REFERENCE TO COPENDING APPLICATIONS

This application is a continuation-in-part of copending application Ser. No. 421,306, filed Dec. 3, 1973, now abandoned, which is a divisional of application Ser. No. 262,849, filed June 14, 1972, now U.S. Pat. No. 3,836,670, which is a continuation-in-part of application Ser. No. 200,517, filed Nov. 19, 1971, now abandoned, which is a continuation-in-part of application Ser. No. 94,983, filed Dec. 3, 1970, now abandoned.

BACKGROUND OF THE INVENTION

This invention relates to compositions of matter classified in the art of chemistry as amine derivatives of 5,8-methano-benzocyclohexane, 5,8-methano-benzocycloheptane, 5,9-methano-benzocycloheptane, 5,9-methano-benzocyclooctane, 5,10-methano-benzocyclooctane, 5,10-methanobenzocyclononane, 5,11-methano-benzocyclononane, 5,11-methanobenzocyclodecane, 5,12-methanobenzocyclodecane, or 5,12-methanobenzocycloundecane, and the non-toxic acid addition salts thereof, which in standard pharmacological tests in animals exhibit analgesic and anti-inflammatory activity, and to processes for making and using such compositions.

5,6,7,8,9,10-Hexahydro-5,9-methano-benzocycloocten-11-amine, 5,6,7,8,9,10-hexahydro-5,9-methano-benzocycloocten-11-one, oxime, and 5,6,7,8,9,10-hexahydro-5,9-methano-benzocyclooctene-11-one have been prepared by Mitsuhashi et al., Chem. Pharm. Bull. (Tokyo), 18, p. 75 (1970). The primary amine was also converted to the corresponding N,N-dimethyl tertiary amine. Although this publication sets forth that the compounds were synthesized as part of a study of structure activity relationships of analgetics, no biological data is given for any compound prepared, and the only reported studies for the compounds are of their spectral properties. No other reports of any practical utility for any of the reference compounds are known.

The structure of the tricyclic reference compounds differs from the tricyclic compounds derived from tetralone of this application in one major particular. This difference is the nature of the carbon atom at the benzylic bridgehead position of the ring system. In the reference compounds this is never other than a tertiary carbon atoms while in the compounds of this application this is always a quaternary carbon atoms. This variation leads to two important distinctions, in addition to the aforesaid lack of any teaching by the reference of practical utility, between the reference compounds and those of this application.

It is currently accepted that the ability of a particular compound to induce analgesia depends inter alia on its ability to fit a particular "receptor site". The steric and spatial relationships in the immediate vicinity of the amino group of known analgesics and their close analogs which do not possess this activity to any significant degree indicates that the area in the immediate vicinity of the amino group is critical for fit with the hypothesized "receptor site". The change to a quaternary carbon atom at a position α to the amino substituent introduces a completely different steric environment near the amino group from that of the compounds of Mitsuhashi.

The change to quaternary carbon also makes the method of synthesis taught by Mitsuhashi inapplicable to any of the compounds of this application. Mitsuhashi's synthesis besides being limited only to benzocyclooctene compounds is limited by the eneamine alkylation used to initiate the sequence. It has been a known advantage of eneamine alkylations of ketonic compounds since their discovery that in contrast to other alkylation methods only one substituent can be introduced in the position α to the carbonyl group. If a substituent is already present at that position a second cannot be introduced.

A discussion representing the generally accepted reasons for the unique behavior of this reaction is set forth by Williamson in Tetrahedron, 3, 314 (1958).

The structure of pyrrolidine eneamines may be depicted as formula XX or XXa:

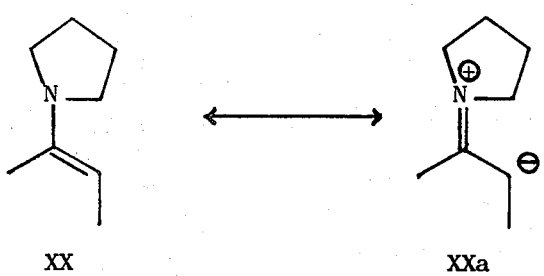

XX          XXa

Form XXa is that involved in the reaction.

Examination of Barton Models (D. H. R. Barton, Chem. and Ind., 1136 (1956)) of α-methylated cyclohexanone (XXI) and 5-phthalimido-2-tetralone (XXII, R=phthalimido) eneamines shows that a combination of steric factors due to the pyrrolidine ring and α-alkyl substitution prevents the introduction of a second alkyl group. These models, when measured, give values of about 1 and 1.4 Angstroms respectively for the distances of the α hydrogen atom of the pyrrolidine ring and the nearest hydrogen atoms of the methyl group when these are equatorial. These are comparable to the "interference radii" of two hydrogen atoms (1.5 Angstroms) Crombie Cromobie (See for example E. A. Braude and F. Sondheimer, J. Chem. Soc., 3754(1955)). The methyl groups must therefore take up the axial position in the active forms XXI and XXII so that equatorial substitution is blocked by the pyrrolidine ring and in the case of XXI axial substitution in the 6-position is also blocked by the axial methyl group. If the α-methyl groups in XXI and XXII were to remain equatorial then coplanarity of the four bonds from the C=N+ group [a necessary condition for the existence of forms XXI and XXII (Dewar, Electronic Theory of Organic Chemistry, Chapter I, Oxford University Press (1948))] would be prevented, C-alkylation would again be inhibited. Of course, in those cases which whic C-alkylation proceeds by rearrangement of N-alkylated forms, arguments involving the stereo chemistry of form (XXa) do not apply. The Mitsuhashi synthesis is not considered to involve an N-alkylated form in the initial substitution.

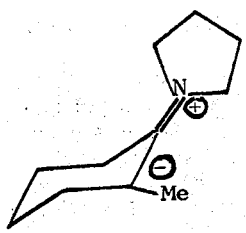
XXI

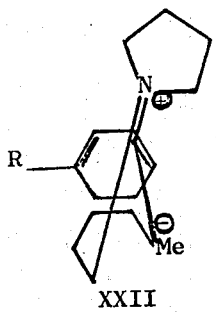
XXII

SUMMARY OF THE INVENTION

The invention sought to be patented in a principal composition of matter aspect resides in the concept of a chemical compound having the structure represented by Formula I:

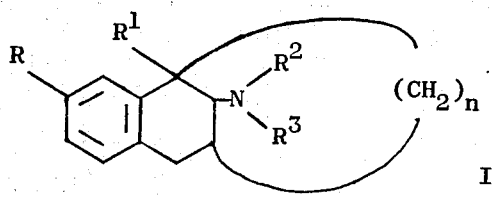

I wherein R is hydrogen, lower alkyl, lower alkyloxy, hydroxy, acyloxy, phen(lower)alkyloxy, halogen, or trifluoromethyl; $R^1$ is lower alkyl, lower alkenyl, or phen(lower)alkyl; $R^2$ is hydrogen, lower alkyl, or phen(lower)alkyl; $R^3$ is hydrogen, lower alkyl, phen(lower)alkyl, lower alkenyl, or alkynyl; and n is an integer from 2 to 6; and the pharmaceutically non-toxic addition salts thereof.

The tangible embodiments of the composition aspect of the invention possess the inherent general physical properties in the acid salt form of being high melting, white crystalline solids, substantially soluble in water and polar organic solvents such as lower aliphatic alcohols and the like. Examination of compounds produced according to the hereinafter described process reveals upon infrared and nuclear magnetic resonance spectroscopic analysis, infrared and nuclear magnetic resonance spectral data confirming the molecular structure hereinbefore set forth. The aforementioned physical characteristics taken together with the microanalytical data, the nature of the starting materials and the mode of synthesis positively confirm the structures of the compositions sought to be patented.

The tangible embodiments of the principal composition aspect of the invention possess the inherent applied use characteristics of exerting an analgesic effect in animals as evidenced by standard pharmacological tests. The analgesic activity of the compositions can be demonstrated by following a modification of the test procedure described by D'Amour and Smith in *Journal of Pharmacology* 72:74 (1941), an accepted test for analgesic agents. In this test rats are administered the compound orally, intraperitoneally or intramuscularly and the time required for response to a pain stimulus caused by a high intensity beam of light shining on the tail measured. The compounds of the invention exhibit analgesic activity in rats at a dose of from 3.15 to 125 mg. per kilogram of body weight orally and intraperitoneally, and from 0.16 to 10.0 mg. per kilogram of body weight intramuscularly.

The invention sought to be patented in a principal process aspect is described as residing in the concept of a sequence of reactions including: introducing by alkylation in the presence of a strong base into the 1 position of a 2-tetralone, which is 1-alkyl, 1-alkenyl, or 1-phen(lower)alkyl substituted, an ω-halo, ω-lower alkyl sulfonyl-, ω-phenylsulfonyl-, or ω-tetrahydropyranyloxyalkyl substituent; if present, hydrolyzing the tetrahydropyranoloxy group and converting the resulting alcohol into a suitable leaving group; treating the ω-halo-, ω-lower alkyl sulfonyl-, or ω-phensulfonyl compound with strong base to effect ring closure; then either reacting the tricyclic ketone directly with ammonia or an amine at elevated temperature with removal of water, and reducing the intermediate imine to produce an amine embodiment of the principal composition aspect; or reacting with hydroxylamine under basic conditions to form an oxime which is reduced to form a primary amine embodiment of the principal composition aspect.

The invention sought to be patented in a subgeneric composition aspect is described as residing in the concept of a chemical compound of Formula I wherein n is 4, or 5.

The tangible embodiments of said subgeneric composition aspect possess the inherent applied use characteristic of exerting analgesic effects in warm-blooded animals as evidenced by pharmacological evaluation by standard test procedures.

The invention sought to be patented in a second subgeneric composition aspect is described as residing in the concept of a chemical compound of Formula I wherein n is 2 or 3.

The tangible embodiments of said subgeneric composition aspect possess the use characteristic of exerting analgesic effects in warm-blooded animals and in addition possess the use characteristic of exerting anti-inflammatory effects in animals as evidenced by standard pharmacologic tests. The anti-inflammatory activity of the composition can be demonstrated by following a test procedure described by Winter et al. in *Proceedings of the Society of Experimental Biology and Medicine:* 111:554 (1962) and by Buttle et al. in Nature 179:629, (1957), a generally accepted test for anti-inflammatory agents. In this test the compound is administered orally as a solution or suspension in distilled water to a group of six rats. After 1 hour edema in the paw of the rats is elicited by injection into the paw of a 1% solution of carrageenin. Paw volume is measured immediately and after 3 hours. The ability of the compounds to reduce the volume of the edema so produced when compared to a like number of control animals is a measure of anti-inflammatory activity. The compounds of the invention exhibit anti-inflammatory activity in rats at a dose of from 50 mg. to 100 mg. per kilogram of body weight.

The invention sought to be patented in a second principle composition aspect resides in the concept of a chemical compound having the structure represented by Formula Ia:

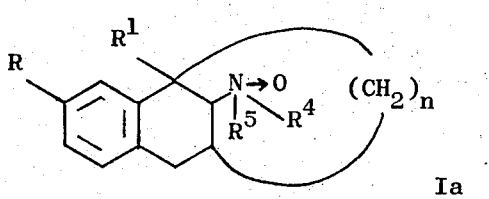

Ia wherein R is as defined hereinabove; $R^1$ is lower alkyl, or phen(lower)alkyl; $R^4$ is lower alkyl; $R^5$ is lower alkyl and n is an integer from 2 to 6; and the pharmaceutically non-toxic addition salts thereof.

The tangible embodiments of said second principle composition aspect of the invention possess the inherent general physical properties in the acid salt form of being high melting, white crystalline solids, substantially insoluble in water and polar organic solvents and the like. Examination of compounds produced according to the hereinafter described process reveals upon infrared and nuclear magnetic resonance spectroscopic analysis, infrared and nuclear magnetic resonance spectral data confirming the molecular structure hereinbefore set forth. The aforementioned physical characteristics taken together with the microanalytical data, the nature of the starting materials and the mode of synthesis positively confirm the structures of the compositions sought to be patented.

The tangible embodiments of said second principle composition aspect of the invention possess the inherent applied use characteristics of exerting an analgesic effect in warm-blooded animals as evidenced by standard pharmacological tests.

The invention sought to be patented in its third composition of matter aspect resides in the concept of a chemical compound having the structure represented by Formula II:

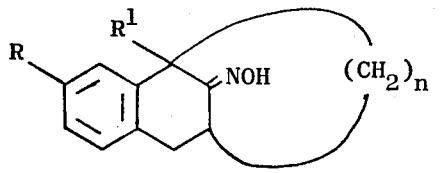

II wherein R, $R^1$, and n are as hereinbefore described.

The tangible embodiments of the third composition aspect of the invention possess the inherent general physical characteristics of being insoluble in water but soluble at elevated temperatures in polar organic solvents such as lower aliphatic alcohols and the like.

Examination of the compounds produced according to the hereinafter described process reveals upon infrared and nuclear magnetic resonance spectroscopic analysis infrared and nuclear magnetic resonance spectral data confirming the molecular structure hereinbefore set forth. The physical characteristics taken together with the nature of the starting materials and the mode of synthesis positively confirm the structure of the compositions sought to be patented.

The tangible embodiments of the third composition aspect of the invention possess the inherent applied use characteristic of being intermediates in the production of the amines of Formula I.

The invention sought to be patented in a fourth composition of matter aspect resides in the concept of a chemical compound having the structure represented by Formula III:

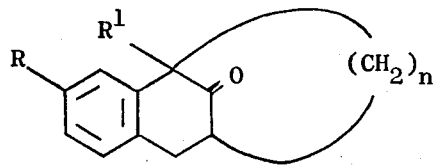

III wherein R, $R^1$ and n are as hereinbefore described.

The tangible embodiments of the fourth composition of matter aspect of the invention possess the inherent general physical characteristic of being high boiling liquids which are substantially insoluble in water but soluble in common organic solvents such as di(lower)alkyl ethers, di(lower)alkyl ketones, lower aliphatic alcohols, chloroform, and the like. Examination of compounds produced according to the hereinafter described process reveals upon infrared and nuclear magnetic resonance spectroscopic analysis, infrared and nuclear magnetic resonance spectral data confirming the molecular structure hereinbefore set forth. The physical characteristics taken together with the nature of the starting materials and the mode of synthesis positively confirm the structure of the compositions to be patented.

The tangible embodiments of the fourth composition aspect of the invention possess the inherent applied use characteristics of being intermediates for the preparation of the amines of Formula I.

The invention sought to be patented in a fifth composition of matter aspect resides in the concept of a chemical compound having the structure represented by Formula IV:

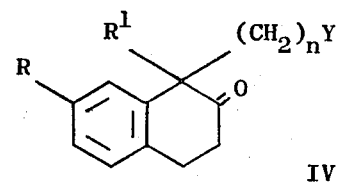

IV wherein R, $R^1$ and n are as hereinbefore described, with the proviso that R is not hydroxyl and Y represents a bromine, chlorine, lower alkyl sulfonyl, phensulfonyl or tetrahydropyranyloxy radical.

The tangible embodiments of the fifth composition of matter aspect of the invention possess the inherent general physical characteristics of being high boiling liquids which are substantially insoluble in water but soluble in common organic solvents such as di(lower)alkyl ethers, di(lower)alkyl ketones, lower aliphatic alcohols, chloroform and the like. Examination of compounds produced according to the hereinafter described process reveals upon infrared and nuclear magnetic resonance spectrographic analysis infrared and nuclear magnetic resonance spectral data confirming the molecular structure hereinbefore set forth. The physical characteristics taken together with the nature of the starting materials and the mode of synthesis positively confirm the structure of the compositions to be patented.

The tangible embodiments of the fifth composition aspect of the invention possess the inherent applied use characteristic of being intermediates in the production of the amines of Formula I.

The invention sought to be patented in a sixth composition of matter aspect resides in the concept of a chemical compound having the structure represented by Formula V:

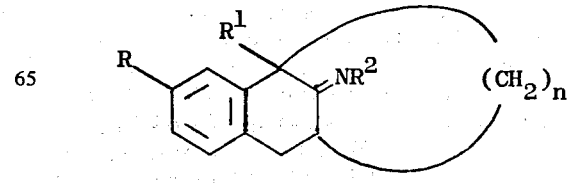

V wherein R, $R^1$, $R^2$ and $n$ are as hereinbefore described.

The tangible embodiments of the sixth composition of matter aspect of the invention possess the inherent general physical characteristics in the acid salt form of being high melting, white crystalline solids, substantially soluble in water and polar organic solvents such as lower aliphatic alcohols and the like. Examination of compounds produced according to the hereinafter described process reveals, upon infrared and nuclear magnetic resonance spectroscopic analysis, infrared and nuclear magnetic resonance spectral data confirming the molecular structure hereinbefore set forth. The aforementioned physical characteristics taken together with the nature of the starting materials and the mode of synthesis positively confirm the structures of the compositions sought to be patented.

The tangible embodiments of the sixth composition aspect of the invention possess the inherent applied use characteristics of being intermediates in the production of the amines of Formula I.

The invention sought to be patented in a seventh composition of matter aspect resides in the concept of a chemical compound having the structure represented by Formula XVI:

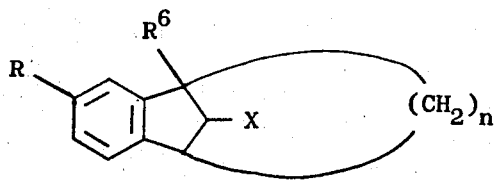

XVI wherein X is:

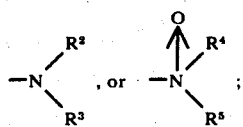

$R^6$ is lower alkyl, or phen(lower)alkyl, and when X is

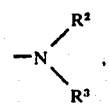

lower alkenyl or hydroxy methyl; and R, $R^2$, $R^3$, $R^4$, $R^5$ and $n$ are as defined hereinabove, and the pharmaceutically non-toxic addition salts thereof.

The tangible embodiments of said seventh composition of matter aspect of the invention possess the inherent general physical properties in the acid salt form of being high melting white crystalline solids, substantially soluble in water and polar organic solvents such as lower aliphatic alcohols and the like. Examination of compounds produced according to the hereinafter described process reveals upon infrared and nuclear magnetic resonance spectroscopic analysis, infrared and nuclear magnetic resonance spectral data confirming the molecular structure hereinbefore set forth. The aforementioned physical characteristics taken together with the microanalytical data, the nature of the starting materials and the mode of synthesis positively confirm the structures of the compositions sought to be patented.

The tangible embodiments of the seventh composition aspect of the invention possess the inherent applied use characteristics of exerting an analgesic effect in warm-blooded animals as evidenced by standard pharmacological tests.

The invention sought to be patented in an eighth composition of matter aspect resides in the concept of a chemical compound having the structure represented by Formula XVII:

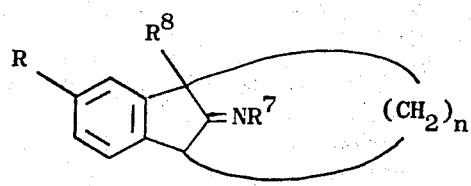

XVII wherein $R^7$ is hydroxy, alkoxy, or when $R^8$ is not alkoxy carbonyl, $R^2$; $R^8$ is $R^6$ or alkoxy carbonyl; and R, $R^2$, $R^6$, and $n$ are as defined hereinabove.

The tangible embodiments of said eighth composition of the invention possess the inherent general physical characteristics of being insoluble in water but soluble at elevated temperatures in polar organic solvents such as lower aliphatic alcohols and the like.

Examination of the compounds produced according to the hereinafter described process reveals upon infrared and nuclear magnetic resonance spectroscopic analysis infrared and nuclear magnetic resonance spectral data confirming the molecular structure hereinbefore set forth. The physical characteristics taken together with the nature of the starting materials and the mode of synthesis positively confirm the structure of the compositions sought to be patented.

The tangible embodiments of the eighth composition aspect of the invention possess the inherent applied use characteristic of being intermediates in the production of the amines of Formula XVI.

The invention sought to be patented in a ninth composition aspect of the invention resides in the concept of a chemical compound having the structure represented by Formula XVIII:

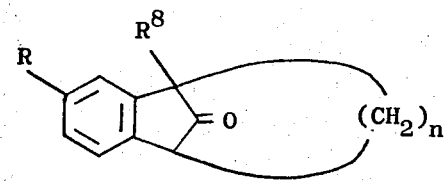

XVIII wherein R, $R^8$ and $n$ are as hereinbefore described.

The tangible embodiments of the ninth composition of matter aspect of the invention possess the inherent general physical characteristics of being high boiling liquids which are substantially insoluble in water but soluble in common organic solvents such as di(lower)alkyl ethers, di(lower)alkyl ketones, lower aliphatic alcohols, chloroform, and the like. Examination of compounds produced according to the hereinafter described process reveals upon infrared and nuclear magnetic resonance spectroscopic analysis, infrared and nuclear magnetic resonance spectral data confirming the molecular structure hereinbefore set forth. The physical characteristics taken together with the nature of the starting materials and the mode of synthesis positively confirm the structure of the compositions to be patented.

The tangible embodiments of the ninth composition aspect of the invention possess the inherent applied use characteristics of being intermediates for the preparation of the amines of Formula XVI.

The invention sought to be patented in a tenth composition of matter aspect resides in the concept of a chemical compound having the structure represented by Formula XIX:

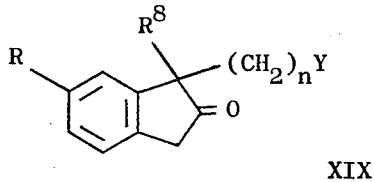

XIX wherein R, $R^8$, Y and $n$ are as hereinbefore described, with the proviso the R is not hydroxyl.

The tangible embodiments of the tenth composition of matter aspect of the invention possess the inherent general physical characteristics of being high boiling liquids which are substantially insoluble in water but soluble in common organic solvents such as di(lower-)alkyl ethers, di(lower)alkyl ketones, lower aliphatic alcohols, chloroform and the like. Examination of compounds produced according to the hereinafter described process reveals upon infrared and nuclear magnetic resonance spectrographic analysis infrared and nuclear magnetic resonance spectral data confirming the molecular structure hereinbefore set forth. The physical characteristics taken together with the nature of the starting materials and the mode of synthesis positively confirm the structure of the compositions to be patented.

The tangible embodiments of the tenth composition aspect of the invention possess the inherent applied use characteristic of being intermediates in the production of the amines of Formula XVI.

The invention sought to be patented in a second process aspect is described as residing in the concept of a process for inducing analgesia in warm-blooded animals by administering to warm-blooded animals, a pharmaceutically effective dose of a compound of Formula I, Formula Ia, or Formula XVI.

As used herein the term "lower alkyl" means a saturated hydrocarbon radical, including the straight and branched radicals having from 1 to 4 carbon atoms, among which are for the purpose of illustration, but without limiting the generality of the foregoing, methyl, ethyl, n-propyl, n-butyl, and i-butyl. The term "lower alkenyl" means an unsaturated hydrocarbon radical, including straight and branched radicals, having from 3 to 5 carbon atoms, among which are for the purposes of illustration but without limiting the generality of the foregoing, allyl, 2-butenyl, 3-methyl-2-butenyl, 2-methyl-2-butenyl, and 2-pentenyl. The term "lower alkynyl" means an unsaturated hydrocarbon radical, containing a triple bond, including straight and branched radicals, having from 3 to 6 carbon atoms, among which are for the purposes of illustration, but without limiting the generality of the foregoing 3-propynyl, 2-butynyl, 1-butyn-3-yl, and 3-methyl-1-butyn-4-yl. The term "phen(lower)alkyl" means a lower alkyl radical as defined hereinabove substituted in a terminal position by a phenyl or a phenyl radical substituted by lower alkyl or lower alkyloxy, among which are for the purposes of illustration but without limiting the generality of the foregoing benzyl, phenethyl, o, m, or p-anisyl, p or m-cumenyl, veratryl, o, m, or p-xylyl. The term "phensulfonyl" means a phenyl or substituted phenyl sulfonic acid radical among which are, for the purposes of illustration, but without limiting the generality of the foregoing, phenyl sulfonyl, or p-toluene sulfonyl. The term acyloxy means either an aliphatic or aromatic carboxylic acid radical of the formula

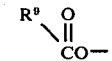

wherein $R^9$ is lower alkyl of 1 to 6 carbon atoms, either straight, or branched chain, or concatenated to form a carbocyclic ring, among which are for the purposes of illustration, but without limiting the generality of the foregoing, acetyloxy, propionyloxy, butyryloxy, i-butyryloxy, cyclohexanecarboxyloxy; or an aromatic nucleus having either an unsubstituted carbocyclic aromatic nucleus of from 6 to 10 carbon atoms, or a carbocyclic aromatic nucleus of from 6 to 10 carbon atoms substituted by lower alkyl, among which are for the purposes of illustration, but without limiting the generality of the foregoing, benzoic, o-, m-, or p-toluic, p- or m-ethylbenzoic.

DESCRIPTION OF THE PREFERRED EMBODIMENTS

In describing the processes for the preparation of the specific embodiments of the invention, reference will be made to FIG. A wherein the compounds are assigned Roman numerals for identification schematically, and wherein is illustrated schematically the reaction sequence for preparing specific primary amine embodiments of Formula I, namely 6,7,8,9,10,11-hexahydro-3-methoxy-5-methyl-5,10-methano-5H-benzocyclononen-12-amine (XI), 12-amino-6,7,8,9,10,11-hexahydro-5-methyl-5,10-methano-5H-benzocyclononen-3-ol (XIV), and 12-amino-6,7,8,9,10,11-hexahydro-5-methyl-5,10-methano-5H-benzocyclononen-3-ol, acetate (XV); specific secondary amine embodiments of Formula I, namely N-allyl-6,7,8,9,10,11-hexahydro-3-methoxy-5-methyl-5,10-methano-5H-benzocyclononen-12-amine (X) and N,5-dimethyl-6,7,8,9,10,11-hexahydro-3-methoxy-5,10-methano-5H-benzocyclononen-12-amine (Xa); specific tertiary amine embodiments of Formula I, namely N-allyl-N,5-dimethyl-6,7,8,9,10,11-hexahydro-3-methoxy-5-methyl-5,10-methano-5H-benzocyclononen-12-amine (XIII); a specific embodiment of Formula II, namely 6,7,8,9,10,11-hexahydro-3-methoxy-5-methyl-5,10-methano-5H-benzocyclononen-12-one, oxime (IX); a specific embodiment of Formula III, namely 6,7,8,9,10,11-hexahydro-3-methoxy-5-methyl-5,10-methano-5H-benzocyclononen-12one (VIII); and a specific embodiment of Formula IV, namely 1-(4-chlorobutyl)-1-methyl-7-methoxy-2-tetralone (VII).

Referring now to FIG. A, the starting materials for the invention, 1-alkyl, 1-alkenyl, or 1-phen(lower)alkyl-2-tetralones, may be prepared from commercially available 2-tetralones, by a well-known alkylation reaction as typically described by Stork and Schulenberg in the *Journal of the American Chemical Society*, 84, 284 (1962). The tetralones are treated with pyrrolidine in an inert solvent such as benzene, and then reacted with the appropriate lower alkyl, lower alkenyl, or phen(-lower)alkyl halide in an inert solvent, such as benzene or dioxane, at elevated temperatures, conveniently the reflux temperature of the solvent employed. They may also be prepared from a suitable commercially available 1-tetralone which may be treated as described by Howell and Taylor in the *Journal of the Chemical Society*, 1958, 1249 with a Grignard reagent, prepared from the appropriate lower alkyl, lower alkenyl, or phen(-lower)alkyl halide, and the resulting 1-substituted dihydro-naphthalene oxidized with peracid.

Syntheses of non-commercially available tetralones are readily available in the literature, e.g. the synthesis of α-tetralone is described in Organic Synthesis, Collective Volume IV, page 898; the synthesis of β-tetralone is described in the same work on page 903; and a general synthesis of β-tetralones is described in Nagata et al. Netherlands Pat. No. 67,09534, Jan. 10, 1968.

The first step in preparing the aforementioned embodiments is the portionwise addition, in the cold, of a strong base, such as a suspension of sodium hydride in benzene, to a stirred solution of 1-methyl-7-methoxy-2-tetralone (VI) and 1-bromo-4-chloro-butane, in dimethyl formamide, followed by a period of stirring at room temperature, to produce compound VII. Compound VII is converted to the bridged tetralone VIII by treatment with a strong base, preferably sodium hydride, in an inert solvent, preferably dimethyl formamide. The bridged tetralone VIII so produced is then used as an intermediate either for the production of the oxime IX or if desired for the production of the secondary amine Xa.

In order to prepare the oxime IX the bridged tetralone VIII is treated with hydroxylamine under basic conditions. The oxime IX may be isolated by conventional means and is used as an intermediate for the production of the primary amine XI. To prepare the amine XI the oxime IX is treated either with hydrogen in the presence of a catalyst, preferably Raney nickel, an ammonium hydroxide, at moderate pressure, preferably 40–50 psi; the hydride reducing agents, for example lithium aluminum hydride; diborane at elevated temperature; or an alkali metal, preferably sodium in an alkanol, for example ethanol or isopropanol. When using catalytic reduction the reaction proceeds stepwise and the corresponding imine of Formula V may be isolated as an intermediate, and then may be reduced to the desired primary amine. The amine XI is isolated by conventional means. To prepare the amine Xa, the bridged tetralone VIII is treated with an excess of methyl amine. The substitution is carried out with removal of water, conveniently in the presence of calcium oxide, at an elevated temperature, preferable 180°–190°C. When the amine has a boiling point below the desired temperature the reaction is conveniently carried out in a sealed pressure vessel. The intermediate imine so produced may be reduced as obtained directly from the substitution reaction. The The amine Xa is produced by treating this imine with either

FIGURE A

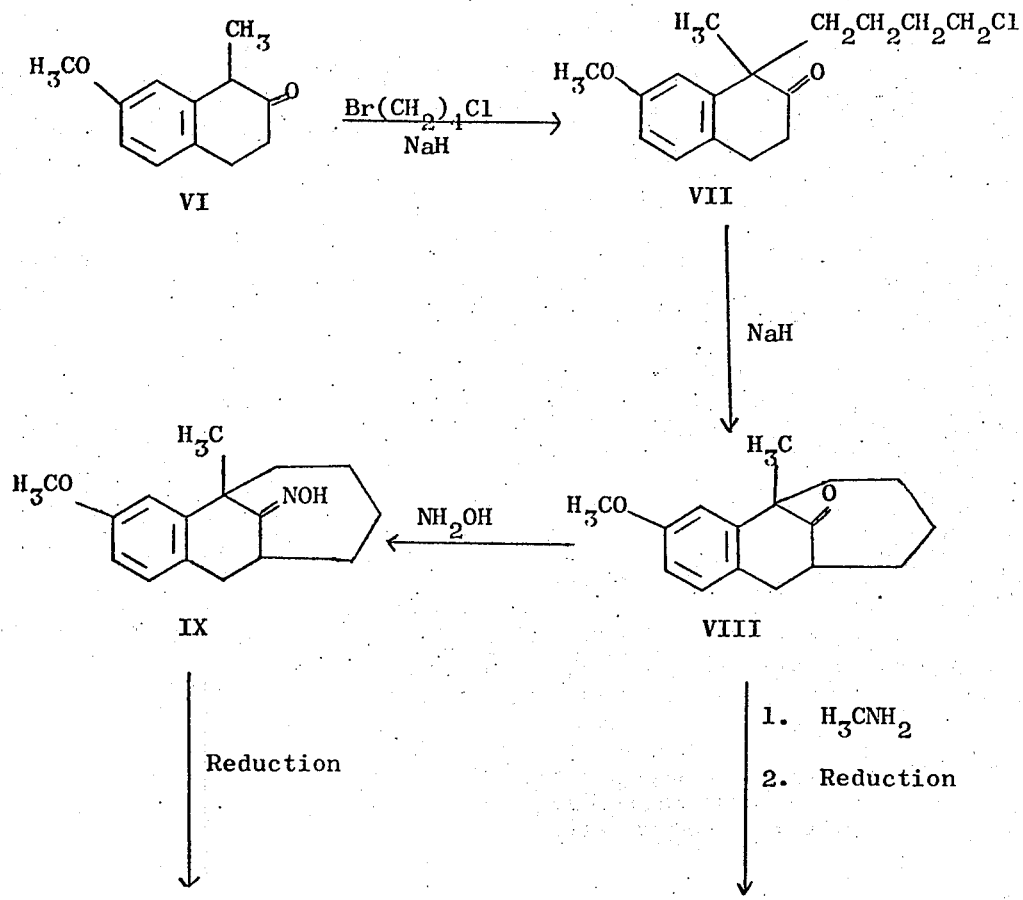

FIGURE A
(Continued)
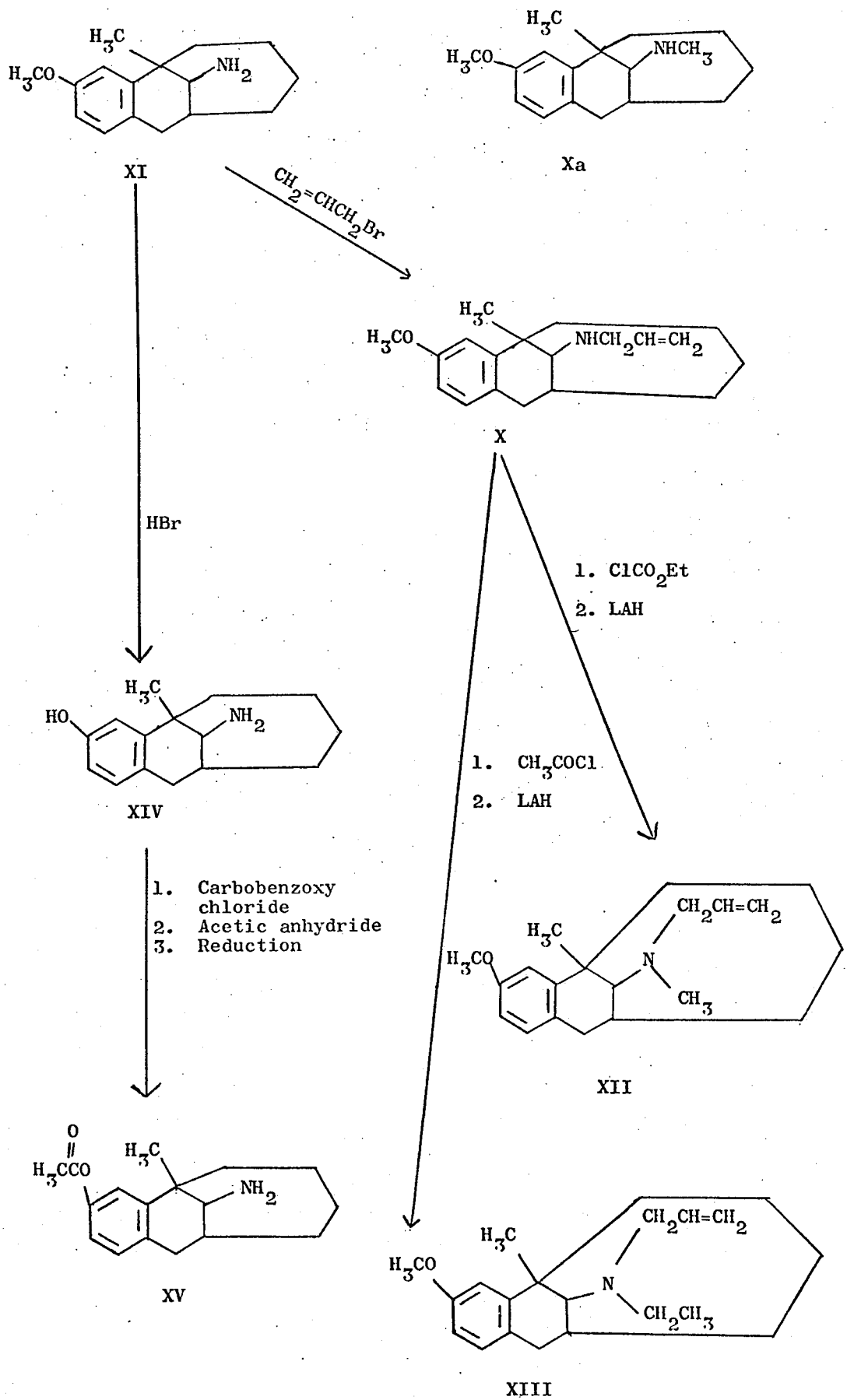

hydrogen in the presence of a catalyst, preferably platinum oxide, at moderate pressure, preferably 40–50 psi; the hydride reducing agents, for example lithium aluminum hydride or sodium borohydride; diborane at elevated temperature, or an alkali metal, preferably sodium, in an alkanol, for example ethanol or isopropanol. The primary amine XI may also be converted to the secondary amine X by substitution reactions well-known in the art of organic chemistry. A convenient method is to treat with one mole equivalent of allyl bromide. The substitution is carried out in the presence of an organic acid acceptor, preferably di-isopropyl ethyl amine, in an organic solvent at a temperature of from about 60° to 140° C. Benzene and xylene are particularly useful solvents but it will be apparent to an organic chemist that any solvent can be used which will not interfere with the course of the reaction. For convenience the reflux temperature of the solvent selected can be employed. The secondary amine X is isolated by conventional methods.

If desired the secondary amine X can be methylated to give the N-methyl tertiary amine XII. A preferred method for the methylation reaction is to first carbethoxylate the secondary amine by treatment with ethyl chloroformate in an unreactive organic solvent, such as methylene chloride or chloroform. For best results, a weak inorganic base, such as sodium bicarbonate or potassium carbonate, is added to the reaction mixture. The temperature of the carbethoxylation reaction is not critical and, for convenience, room temperature is used. It will be obvious to one skilled in organic chemistry that for the purposes of this reaction other halo formate esters would be equivalent to ethyl chloroformate. The carbethoxylated amine is then reacted with a reducing agent, preferably lithium aluminum hydride, in an inert solvent, preferably ether or tetrahydrofuran, to afford the N-methyl tertiary amine XII which is isolated by standard procedures.

A preferred method of preparation of the tertiary amine XIII is to first acylate the secondary amine X with acetyl chloride in a basic organic solvent, preferably pyridine, at an elevated temperature, conveniently the reflux temperature of the solvent selected. The acylated amine is then reacted with a reducing agent, preferably lithium aluminum hydride, in an inert solvent preferably ether or tetrahydrofuran, to afford the tertiary amine XIII which is isolated by standard techniques.

The primary amine XI which bears a lower alkyloxy substituent can be hydrolyzed to the phenolic compound XIV. A particularly useful method is to treat the primary amine with 48% aqueous hydrobromic acid at elevated temperature, conveniently reflux temperature. The crystalline product is isolated by standard techniques. It will be obvious to one skilled in the art of organic chemistry that the hydrolysis reaction may be performed on the bridged tetralone VIII and that the phenolic compound so formed would then be the full equivalent of all other compounds not bearing such a substituent in all subsequent reactions.

The phenolic amine XIV may be acetylated to produce the acetyl derivative XV. A skilled organic chemist will recognize that in order to acetylate the phenolic function a primary or secondary amine must first be reacted with a suitable protecting group. Carbobenzoxy chloride is particularly convenient for this purpose. The protected derivative is then treated with acetic anhydride and the protecting group removed, conveniently, in the case of the carbobenzoxy group by hydrogenolysis. It will be obvious to a skilled organic chemist that any desired acylation reagent may be substituted for the acetic anhydride. The acylation reaction may also be accomplished by exposure of the phenolic amine, suitably distributed on an inert carrier, conveniently potassium bromide powder, to a suitably volatile acylating agent, in the vapor state, at temperatures moderately higher than room temperature, conveniently 40°–70° C.

While the processes of the invention have been specifically described with reference to the drawing which illustrates their application to 1-methyl-7-methoxy-2-tetralone it will be readily apparent to one skilled in the art of organic chemistry that the processes will be equally applicable to tetralones bearing, in the 1 and 7 positions, other substituents contemplated within the scope of the invention. Similarly it will be obvious to vary the chain length of the polymethylene compound in order to produce the variously sized ring systems encompassed by the invention. A skilled chemist will readily recognize that, in addition to the $\alpha,\omega$-dihalopolymethylene, any polymethylene compound of the desired chain length, which bears, as substituents in the terminal positions, suitable leaving groups, such as (lower)alkylsulfonyl or phensulfonyl, or one such leaving group and a group, such as tetrahydropyranyloxy which may be readily converted to a leaving group, may be utilized in the initial cycloalkylation process. The substitution of other strong bases, such as alkali metal alkoxides, in suitable solvents, for the illustrated sodium hydride will also be apparent to one skilled in the art. It will be obvious to one skilled in the art that, if the $\alpha,\omega$-disubstituted polymethylene does not bear a tetrahydropyranyl substituent, the complete cycloalkylation may be performed without isolation of the intermediate, compound VII. One skilled in the art will recognize that it is possible to substitute anhydrous ammonia for methyl amine in the imination of compound VIII and that reduction will then give compound XI. The substitution of other lower alkyl, and phen(lower)alkyl amines, for methylamine, to give secondary amines analogous to compound Xa will similarly be apparent to one skilled in the art. Other lower alkyl halides, lower alkenyl halides, phen(lower)alkyl halides, or lower alkynyl halides may be substituted for allyl bromide in the treatment of compound XI to obtain the secondary amines encompassed by the invention. Similarly other lower alkanoyl, lower alkenoyl, pheny(lower)alkanoyl or lower alkynyl halides may be used in the preparation of the tertiary amine embodiments of the invention.

The amine oxides of Formula Ia are prepared by oxidation, conveniently with an organic peracid, of the di(lower)alkyl tertiary amine embodiments of Formula I.

One knowledgeable in the art of organic chemistry will recognize that 1-alkyl-substituted 2-indanones and 2-benzsuberones can be cycloalkylated in a fashion similar to that described for the cycloalkylation of 1-alkyl substituted 2-tetralones. The compounds so formed can then be further treated by the processes described hereinabove to produce derivatives which are the full equivalents of the compounds of Formula I described herein.

The substituted tetralones described hereinabove and their equivalent indanone and benzsuberone analogues may be substituted at various other positions on the aromatic ring with such radicals as lower alkyl, lower alkyloxy, halo and trifluoromethyl and these may be employed as starting materials in the initial cycloalkylation reactions and such compounds can then be treated by the processes described hereinabove, to produce amino derivatives bearing these variously located substituents.

Preparation of the indanones of Formula XVI may also be accomplished by cyclization of appropriate known o-phenylene diacetic acid diesters to produce 1-alkoxycarbonyl-2-indanones. Alkylation to produce the 1-alkoxy carbonyl-indanones of Formula XIX may be accomplished by standard alkylation techniques. Alternatively the keto group of the alkoxy carbonylindanone may be treated with a suitable ketone protecting reagent, such as ethylene glycol, a lower alkyl, lower alkenyl, or phen(lower)alkyl group may be introduced into the 1-position by standard alkylation techniques, the protective group removed from the ketone, the ester function hydrolyzed, and the carbonyl group eliminated by decarboxylation. The resulting lower alkyl, lower alkenyl, or phen(lower)alkyl-2-indanone may then be treated similarly to the corresponding tetralones to produce the lower alkyl, loer alkenyl or phen(lower)alkyl indanones of Formula XIX. Cycloalkylation to the benzobicyclic system of Formula XVIII may be accomplished as described for the corresponding tetralones of Formula IX. Preparation of the imino derivatives of the benzobicyclic ketones derived from the above described indanones may be accomplished in a fashion similar to that described for the preparation of the imino derivatives of the banzobicyclic ketones derived from tetralones. A skilled organic chemist will of course recognize that the alkoxy carbonyl substituted benzobicyclic ketones may be converted to oximino derivatives but that treatment with ammonia or primary amine will result in side reactions with the alkoxy carbonyl group.

The skilled organic chemist will of course not use catalytic reduction methods involving the use of ammonia or primary amines.

The alkoxy carbonyl benzobicyclic ketone may, if desired, be treated with a suitable ketone protecting reagent, such as ethylene glycol, the alkoxy carbonyl group may then be reduced to a hydroxy methyl group, and the keto group regenerated. This compound may then be converted into the hydroxy methyl imino compounds of Formula XVII by the above described methods.

Reduction of the oximes or imines of Formula XVII to the amines of Formula XVI may be accomplished by the same reduction methods as used to prepare the amines of Formula I. Those embodiments of Formula XVII containing an alkoxycarnbonyl will, of course, simultaneously be converted to the embodiments of Formula XVI which have a hydroxy(lower)alkyl substituent. If desired the hydroxyl group may be removed by standard means, such as tosylation and reduction with lithium aluminum hydride. Ordinarily this process will result in an N-tosyl amine from which the free amine may be recovered by hydrolysis. The variously other substituted amines of Formula XVI may be prepared from appropriate primary or secondary amines or embodiments of Formula XVI by processes similar to those described for the preparation of the variously substituted amines of Formula I.

It will be obvious to one skilled in the art of chemistry that the benzobicyclic ketones of Formula III and Formula XVIII will be produced as racemic mixtures, and that reduction of either oximes of Formula II and Formula XVII or imines of Formula V and Formula XVII will yield the amines of Formula I and Formula XVI as diastereomers. The separation of the diastereomeric pairs and their resolution into enantiomers, if desired, may be accomplished by well-known procedures. The diastereomers, enantiomers and mixtures thereof are all included within the scope of this invention.

It is convenient in the present application to distinguish pairs of diastereomers by specifying the orientation of the amino group. A number of conventional systems of nomenclature for specifying the orientation are suitable, and selection of a particular system is a matter of convenience. Because of its greater specificity and more general applicability, a system enabling specification of the relative orientation of all substituents on the tetralin ring system has been adopted for use in this application. In this system the tetralin ring is projected on a plane. Those substituents extending below the plane are designated $\alpha$, and those extending above the plane are designated $\beta$.

In the process for the use of the amines of Formula I and Formula XVI or pharmaceutical acceptable salts thereof, they may, if desired, be formulated with pharmaceutically acceptable carriers in accordance with methods well-known in the art.

It will be obvious to those skilled in the art that N-oxides of the dialkyl substituted tertiary amines of Formula XVIa may be prepared in a fashion similar to that described for the preparation of the N-oxides of Formula Ia. These N-oxides are the full equivalents of those embodiments of the invention specifically described.

An alternate synthesis of the amines of Formula I and Formula XVI is through the preparation of a compound of the formula:

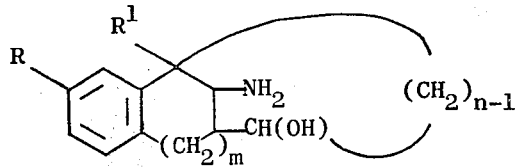

wherein R, $R^1$, and $n$ are as defined hereinabove; and $m$ is 0 or 1, as described by Wiesner, Chau and Demerson in Tetrahedron Letters, 1965, page 2893, followed by either dehydration and hydrogenation of the resulting double bond, or tosylation and cleavage of the tosyl group. This route is the preferred method of synthesis for those embodiments wherein $n$ is 2 or 6.

The tangible embodiments of the principal composition aspect have been found to possess the additional applied use characteristic of exerting morphine antagonism effects in animals when tested in standard pharmacological evaluation procedures. The morphine antagonism effects can be demonstrated by administering the compound to morphine addicted monkeys. A morphine antagonist precipitates morphine withdrawal symptoms. The morphine antagonism effect can also be demonstrated by dosing groups of three male Charles River rats subcutaneously with morphine at 75 mg/Kg of base. The degree of narcosis induced by the morphine is measured at 15 and 30 minutes after injection.

Criteria are loss of righting reflex, tail and body rigidity and respiratory depression. Test compounds are administered intramuscularly, 40 minutes after the morphine. The degree of antagonism is measured at 20 minute intervals for 2 hours. Nalorphine, at 2 mg/kg, serves as a positive control while one group of morphinized rats in each determination receives no antagonist and serves as negative controls. Reversal of the loss of righting reflex constitutes a positive response.

The following examples illustrate the best mode contemplated by the inventors for preparing the compositions of the invention.

EXAMPLE I 1-(4-Chlorobutyl)-1-Methyl-7-Methoxy-2-Tetralone

1-Methyl-7-methoxy-2-tetralone (57 g.), tetramethylene chlorobromide (200 g.) and dimethyl formamide (250 ml.) are introduced into a two liter reaction vessel which is fitted with a condenser and drying tube, a mechanical stirrer, a nitrogen inlet, a thermometer, and a soft rubber stopper. After this solution is cooled to 10° C. a suspension of sodium hydride (approximately 8 g. freed of mineral oil by washing with benzene) in benzene (100 ml.) is added slowly in 10 ml. portions, through the rubber stopper with the aid of a syringe. The temperature is maintained between 12° and 20° for the 1.5 hour addition period. The reaction is then allowed to warm to room temperature, stirred for 3½ hours, and poured into ice water (1.5 l.). The layers are separated, the aqueous phase extracted with ether, the combined organic phases washed with saturated saline, dried over sodium sulfate and the organic solvents removed under reduced pressure. Distillation of the residue yields the title product (62.5 g.) b.p. 155°–185° C. (approximately 0.3 mm.).

I. R. Analysis: 5,85, 7.95 $\mu$.

EXAMPLE II 1-(3-Bromopropyl)-1-Methyl-2-Tetralone

Sodium hydride (0.75 g.) washed free of mineral oil is added in small portions, over a period of 45 minutes, to a well stirred solution of 1-methyl-2-tetralone (4.8 g.) and 1,3-dibromopropane (24 g.) in benzene (100 ml.) while maintaining the temperature at 25° C. The mixture is stirred at room temperature for 1 hour and heated at reflux for 2 hours. When cool 2 drops of acetic acid are added and the mixture clarified by filtration through diatomaceous earth. Concentration of the filtrate and distillation of the resulting residue gives the title product (4.5 g.) b.p. 130°–135° C. (0.1 mm.); 2,4-dinitrophenylhydrazone m.p. 146°–148° C.

Analysis for: $C_{20}H_{21}N_4O_4Br$ Calculated: C, 52.07; H, 4.59; N, 12.14; Br, 17.32 Found: C, 51.87; H, 4.64; N, 11.97; Br, 17.12.

EXAMPLE III 1-(3-Bromopropyl)-1-Methyl-7-Methoxy-2-Tetralone

Using a procedure analogous to that described in Example II for the preparation of 1-(3-bromopropyl-1-methyl)-2-tetralone there is obtained from 1-methyl-7-methoxy-2-tetralone (11.4 g.) and 1,3-dibromopropane (24 ml.), 6.7 g. of the title product, b.p. 135°–145° C. (1 mm.).

I. R. Analysis: 5.8, 8.0 $\mu$.

EXAMPLE IV 1-(5-Bromopentyl)-1-Methyl-2-Tetralone

Using a procedure analogous to that described in Example I for the preparation of 1-(4-chlorobutyl)-1-methyl-7-methoxy-2-tetralone there is obtained from 1-methyl-2-tetralone (20.0 g., 0.125 mole), 1,5-dibromopentane (115.0 g., 0.5 mole), and sodium hydride (6.06 g., 0.1375 mole of a 54.5% dispersion in mineral oil) in dimethylformamide (100 ml.), 19.8 g. (54 %) of the title product b.p. 155°–175° C. (0.3 mm.).

I. R. Analysis: 3.45, 5.85 $\mu$.

EXAMPLE V 1-(5-Bromopentyl)-1-Methyl-7-Methoxy-2-Tetralone

Using a procedure analogous to that described in Example I for the preparation of 1-(4-chlorobutyl)-1-methyl-7-methoxy-2-tetralone there is obtained from 1-methyl-7-methoxy-2-tetralone (150.0 g., 0.788 mole), 1,5-dibromopentane (707 g., 3.06 mole), and sodium hydride (37.1 g., 0.842 mole of a 54.5% dispersion in mineral oil) in dimethylformamide (600 ml.). 182 g. (68.1% of the title product b.p. 185°–198° C. (1.0 mm.).

I. R. Analysis: 3.5, 5.80, 7.9 $\mu$.

EXAMPLE VI 1-(4-Chlorobutyl)-1-Ethyl-7-Methoxy-2-Tetralone

A. Using a procedure analogous to that described in Example I for the preparation of 1-(4-chlorobutyl)-1-methyl-7-methoxy-2-tetralone there is obtained from 35 g. of 1-ethyl-7-methoxy-2-tetralone; 37.4 g. of the title product b.p. 160°–173° C. (0.4 mm.).

I. R. Analysis: 5.83, 8.0 $\mu$.

B. Clean sodium pellets (2.3 g.) are dissolved, while stirring magnetically under $N_2$, in absolute ethanol (50 ml.). After cooling to 20°–25° C. 1-ethyl-7-methoxy-2-tetralone (20.5 g.) in dry ethanol (50 ml.) is added over a period of 30 minutes. After stirring 30 minutes this solution is added dropwise to a stirred solution of 1,4-dibromobutane (44.0 g.) in dry ethanol (60 ml.) while maintaining the temperature at 10°–15° C. After stirring four hours at this temperature the reaction is allowed to warm to 20°–25° C. while continuing to stir an additional 12 hours. After chilling below room temperature precipitated solids are removed by filtration with aid of diatomaceous earth. Concentration of the filtrate under reduced pressure, partitioning the residue so obtained between ether and water, washing the ether layer with saline, drying, concentrating under reduced pressure and distilling under vacuum gives the title product (16 g.) b.p. 165°–175°(0.2 mm.).

Example VII 1-(4-Chlorobutyl)-1-Methyl-5-Methoxy-2-Tetralone

Using a procedure analogous to that described in Example I for the preparation of 1-(4-chlorobutyl)-1-methyl-7-methoxy-2-tetralone there is obtained from 1-methyl-5-methoxy-2-tetralone (45 g.), 40.5 g. of the title product, b.p. 150°–160° C. (0.15 mm.).

I. R. Analysis: 5.82, 7.9 $\mu$.

EXAMPLE VIII 1-(4-Chlorobutyl)-1-Methyl-6-Methoxy-2-Tetralone

Using a procedure analogous to that described in Example I for the preparation of 1-(4-chlorobutyl)-1-methyl-7-methoxy-2-tetralone there is obtained from 1-methyl-6-methoxy-2-tetralone (36 g.) and tetramethylene chlorobromide (140 g.), 30.5 g. of the title product, b.p. 165°–175° C. (0.4 mm.).

I. R. Analysis: 5.85, 8.0 $\mu$.

EXAMPLE IX

To prepare: 1-benzyl-1-(4-chlorobutyl)-2-tetralone react 1-benzyl-2-tetralone with 1-bromo-4-chlorobutane as taught in Example I.

To prepare: 1-benzyl-1-(4-chlorobutyl)-7-methoxy-2-tetralone react 1-benzyl-7-methoxy-2-tetralone with 1-bromo-4-chlorobutane as taught in Example I.

EXAMPLE X 6,7,8,9,10,11-Hexahydro-3-Methoxy-5-Methyl-5,10-Methano-5H-Benzocyclononen-12-One To a 2 liter reaction vessel, fitted with a mechanical stirred, a dropping funnel, a condenser and drying tube, a thermometer, a nitrogen inlet and a soft rubber stopper is introduced sodium hydride (13 g., 0.27 mole of 50% dispersion in mineral oil) which is then washed with benzene to remove the mineral oil. Dimethylformamide (750 ml.) is then added and 1-(4-chlorobutyl)-1-methyl-7-methoxy-2-tetralone (62.5 g., 0.22 mole in dimethyl formamide (150 ml.) is added dropwise, while stirring vigorously and maintaining the temperature between 30° and 35° C. The reaction is stirred and heated to 80° to 85° C. for 2.5 hours, stirred at room temperature overnight and poured into ice water (2.0 liter). After acidification with hydrochloride acid (concentrated) the oil which separates is extracted into ether. The extract is washed with saturated saline and dried over sodium sulfate. The solvent is removed under reduced pressure and the residue distilled to give the title product (32.5 g.), b.p. 130° to 135° C. (0.25 mm.), I. R. Analysis: 5.8, 8.0 $\mu$.

EXAMPLE XI 5,6,7,8,9,10-Hexahydro-3-Methoxy-5-Methyl-5,9-Methano-Benzocycloocten-11-One Using a procedure analogous to that described in Example X for the preparation of 6,7,8,9,10,11-hexahydro-3-methoxy-5-methyl-5,10-methano-5H-benzocycloocten-12-one there is obtained from 1-(3-bromopropyl)-1-methyl-7-methoxy-2-tetralone in 74% yield the title product, b.p. 118° to 121° C. (0.05 mm.). A sample is converted to the semicarbazone, m.p. 223° to 225° C.

Analysis for: $C_{16}H_{21}N_3O_2$ Calculated: C, 66.87; H, 7.37; N, 14.62 Found: C, 66.73; H, 7.51; N, 14.74.

EXAMPLE XII 5,6,7,8,9,10-Hexahydro-5-Methyl-5,9-Methanobenzocycloocten-11-One Using a procedure analogous to that described in Example X for the preparation of 6,7,8,9,10,11-hexahydro-3-methoxy-5-methyl-5,10-methano-5H-benzocyclononen-12-one there is obtained from 1-(3-bromopropyl)-1-methyl-2-tetralone (4.0 g.) treated with sodium hydride (1 g.); 1.4 g. of the title product, b.p. 122° to 130° C. (0.1 mm.). A sample is converted to the semicarbazone and crystallized from acetonitrile, m.p. 250° to 251° C.

Analysis for: $C_{15}H_{19}N_3O$ Calculated: C, 70.00; H, 7.44; N, 16.33 Found: C, 70.30; H, 7.39; N, 16.48.

EXAMPLE XIII

5-Methyl-5,6,7,8,9,10,11,12-Octahydro-5,11-Methano-Benzocyclodecen-13-One

Using a procedure analogous to that described in Example X for the preparation of 6,7,8,9,10,11-hexahydro-3-methoxy-5-methyl-5,10-methano-5H-benzocyclononen-12-one there is prepared from 1-methyl-1-(5-bromopentyl)-2-tetralone (19.8 g., 0.0675 mole) and sodium hydride (3.57 g., 0.081 mole, of a 54.5% dispersion in mineral oil) in dimethylformamide (250 ml.); 6.2 g. (40.4%) of the title product, b.p. 126° to 135° C. (0.3 mm.).

I. R. Analysis: 3.45, 5.9 $\mu$.

EXAMPLE XIV

5-Methyl-3-Methoxy-5,6,7,8,9,10,11,12-Octahydro-5,11-Methano-benzocyclodecen-13-One A. Using a procedure analogous to that described in Example X for the preparation of 6,7,8,9,10,11-hexahydro-3-methoxy-5-methyl-5,10-methano-5H-benzocyclononen-12-one there is obtained from 1-methyl-1-(5-bromopentyl)-7-methoxy-2-tetralone (90.0 g., 0.264 mole), and sodium hydride (12.87 g., 0.292 mole, of 54.5% dispersion in mineral oil) in dimethylformamide (750 ml.); 42.7 g. (62.4%) of the title product, b.p. 150° to 175° C. (0.5 mm.).

I. R. Analysis: 3.0, 3.4, 5.9, 8.01 $\mu$.

B. Oil-free sodium hydride (5.28 g.) in benzene (50 ml.) is added to a stirred mixture of 1,5-dibromopentane (184 g.) and 1-methyl-7-methoxy-2-tetralone (32 g.) in dry benzene (300 ml.). Stirring is continued for 12 hours at 25° and at reflux for an additional 15 hours. The mixture is cooled, sodium hydride (5.8 g.) in 50 ml. benzene added, stirring continued at 25° for 10 hours, and at reflux for 12 additional hours. After cooling excess base is neutralized with concentrated hydrochloric acid and the inorganic solids which precipitate are removed by filtration. Washing and filtrate with saline, drying over sodium sulfate, concentrating and vacuum distilling gives an oil (21 g.), b.p. 160°–190° C. (0.5 mm.) containing 6.5 g. (27%) of the title product by vapor phase chromatography (3% OVI, C200-225-250).

EXAMPLE XV 6,7,8,9,10,11-Hexahydro-2-Methoxy-5-Methyl-5,10-Methano-5H-Benzocyclononen-12-One Using a procedure analogous to that described in Example X for the preparation of 6,7,8,9,10,11-hexahydro-3-methoxy-5-methyl-5,10-methano-5H-benzocyclononen-12-one, there is obtained from 30.5 g. of 1-(4-chlorobutyl)-1-methyl-6-methoxy-2-tetralone 15 g. of the title product, b.p. 140° to 145° C. (0.5 mm.).

I. R. Analysis: 5.82, 8.05 $\mu$.

EXAMPLE XVI 6,7,8,9,10,11-Hexahydro-1-Methoxy-5-Methyl-5,10-Methano-5H-Benzocyclononen-12-One Using a procedure analogous to that described in Example X for the preparation of 6,7,8,9,10,11-hexahydro-3-methoxy-5-methyl-5,10-methano-5H-benzocyclononen-12-one, there is obtained from 40.5 g. of 1-(4-chlorobutyl)-1-methyl-5-methoxy-2-tetralone, 21.5 g. of the title product, b.p. 130° to 135° C. (0.3 mm.).

I. R. Analysis: 5.78, 7.9 $\mu$.

EXAMPLE XVII

5-Ethyl-6,7,8,9,10,11-Hexahydro-3-Methoxy-5,10-Methano-5H-Benzocyclononen-12-One Using a procedure analogous to that described in Example X for the preparation of 6,7,8,9,10,11-hexahydro-3-methoxy-5-methyl-5,10-methano-5H-benzocyclononen-12-one there is obtained from 37.4 g. of 1-(4-chlorobutyl)-1-ethyl-7-methoxy-2-tetralone, 22.2 g. of the title product, b.p. 138° to 142° C. (0.35 mm.).

I. R. Analysis: 5.85, 8.0 μ.

EXAMPLE XVIII

To prepare: 6,7,8,9,10,11-hexahydro-5-benzyl-5,10-methano-5H-benzocyclononen-12-one, treat 1-benzyl-1-(4-chlorobutyl)-2-tetralone with sodium hydride as taught in Example X.

To prepare: 5-benzyl-3-methoxy-6,7,8,9,10,11-hexahydro-5,10-methano-5H-benzocyclononen-12-one, treat 1-benzyl-1-(4-chlorobutyl)-7-methoxy-2-tetralone with sodium hydride as taught in Example X.

EXAMPLE XIX 6,7,8,9,10,11-Hexahydro-3-Methoxy-5-Methyl-5,10-Methano-5H-Benzocyclononen-12-One, Oxime A. 6,7,8,9,10,11-Hexahydro-3-methoxy-5-methyl-5,10-methano-5H-benzocyclononen-12-one (0.2 g.), hydroxylamine hydrochloride (0.5 g.) 5% sodium hydroxide (6 ml.) and ethanol (2 ml.) are heated at reflux for 4 hours. The reaction is cooled and diluted with water. The supernatant is decanted from the oil which separates. The oil is washed several times with water and is then treated with 2-propanol from which the title product crystallizes, m.p. 174° to 176° C.

Analysis for: $C_{16}H_{21}NO_2$ calcuated: C, 74.1; H, 8.16; N, 5.40 Found: C, 74.38; H, 8.10; N, 4.98.

I. R. Analysis: 3.2, 6.2, 8.1 μ.

B. Hydroxylamine hydrochloride (14 g., 0.2 mole) in methanol (250 ml.) is mixed with sodium acetate (165 g., 0.2 mole) in methanol (200 ml.). After standing one hour the solution is filtered and to it is added 6,7,8,9,10,11-hexahydro-3-methoxy-5-methyl-5,10-methano-5H-benzocyclononen-12-one (10 g., 0.04 mole). The solution is heated under reflux 5 hours, concentrated in volume to approximately 200 ml. Cooling, filtration, washing with methanol and drying gives the title product (8.0), m.p. 174° to 176° C.

C. 6,7,8,9,10,11-Hexahydro-3-methoxy-5-methyl-5,10-methano-5H-benzocyclononen-12-one (20.0 g., 0.082 mole), and hydroxylamine hydrochloride (28.5 g., 0.410 mole) in pyridine (150 ml.) are stirred at reflux for 24 hours. The mixture is cooled and concentrated. The residue is extracted with ether (750 ml.) in several portions and the extracts are successively washed with water, dilute hydrochloric acid, water and saline solution, then dried over anhydrous magnesium sulfate, the solvent removed in vacuo and the residue crystallized from boiling isopropanol to give the title product (6.0 g.), m.p. 167° to 171° C. A second crop was obtained 1.08 g. Total yield is 33%.

EXAMPLE XX

5Methyl-5,6,7,8,9,10,11,12-Octahydro-5,11-Methano-Benzocyclodecen-13-One, Oxime

Using a procedure analogous to that described in Example XIX, Method C, for the preparation of 6,7,8,9,10,11-hexahydro-3-methoxy-5-methyl-5,10-methano-5H-benzocyclononen-12-one, oxime there is obtained from 5-methyl-5,6,7,8,9,10,11,12-octahydro-5,11-methano-benzocyclodecen-13-one (3.9 g., 0.0171 mole) and hydroxylamine hydrochloride (8.55 g., 0.123 moles) in pyridine (20 ml.), after recrystallization from isopropanol, 1.27 g. of the title product, m.p. 122°–127°.

I. R. Analysis: 3.15, 3.45, 6.1 μ.

EXAMPLE XXI 5,6,7,8,9,10-Hexahydro-3-Methoxy-5-Methyl-5,9-Methano-Benzocycloocten-11-One, Oxime By a procedure analogous to that described in Example XIX, Method A, for the preparation of 6,7,8,9,10,11-hexahydro-3-methoxy-5-methyl-5,10-methano-5H-benzocyclononen-12-one, oxime there is obtained from 5,6,7,8,9,10-hexahydro-3-methoxy-5-methyl-5,9-methanobenzocycloocten-11-one (0.5 g.) and hydroxylamine hydrochloride (6.5 g.), 3.9 g. of product after trituration with hexane, m.p. 138°–142° C. Recrystallization from isopropanol-water gives the title product, m.p. 146°–148° C.

Analysis for: $C_{15}H_{19}NO_2$ Calculated: C, 73.44; H, 7.81; N, 5.71 Found: C, 73.11; H, 8.03; N, 5.61.

EXAMPLE XXII

5-Methyl-3-Methoxy-5,6,7,8,9,10,11,12-Octahydro-5,11-Methano-Benzocyclodecen-13-One, Oxime Using a procedure analogous to that described in Example XIX, Method C for the preparation of 6,7,8,9,10,11-hexahydro-3-methoxy-5-methyl-5,10-methano-5H-benzocyclononen-12-one, oxime there is obtained from 5-methyl-5,6,7,8,9,10,11-octahydro-5,11-methano-benzocyclodecen-13-one (42.6 g., 0.165 mole), and hydroxylamine hydrochloride (57.3 g., 0.824 mole) in pyridine (300 ml.); 18.9 g. (42%) of the title product, m.p. 152°–158° C.

Analysis for: $C_{17}H_{13}N_2O_2$ Calculated: C, 74.69; H, 8.48; N, 4.12 Found: C, 75.25; H, 8.64; N, 4.72.

EXAMPLE XXIII 6,7,8,9,10-Hexahydro-2-Methoxy-5-Methyl-5,10-Methano-5H-Benzocyclononen-12-One, Oxime Using a procedure analogous to that described in Example XIX, Method B, for the preparation of 6,7,8,9,10,11-hexahydro-3-methoxy-5-methyl-5,10-methano-5H-benzocyclononen-12-one, oxime there is obtained from 11.5 g. of 6,7,8,9,10,11-hexahydro-2-methoxy-5-methyl-5,10-methano-5H-benzocyclononen-12-one (5.0 g.) of the title product, m.p. 130°–135° C.

I. R. Analysis: 3.1; 6.0 μ.

EXAMPLE XXIV 6,7,8,9,10,11-Hexahydro-1-Methoxy-5-Methyl-5,10-Methano-5H-Benzocyclononen-12-One, Oxime Using a procedure analogous to that described in Example XIX, Method B, for preparation of 6,7,8,9,10,11-hexahydro-3-methoxy-5-methyl-5,10-methano-5H-benzocyclononen-12-one, oxime there is obtained from 21.5 g. of 6,7,8,9,10,11-hexahydro-1-methoxy-5-methyl-5,10-methano-5H-benzocyclononen-12-one, 10.9 g. of the title product, m.p. 154°–160° C.

I. R. Analysis: 3.1-3.2; 6.0 μ.

EXAMPLE XXV

5-Ethyl-6,7,8,9,10,11-Hexahydro-3-Methoxy-5,10-Methano-5H-Benzocyclononen-12-One, Oxime Using a procedure analogous to that described in Example XIX, Method C, for the preparation of 6,7,8,9,10,11-hexahydro-3-methoxy-5-methyl-5,10-methano-5H-benzocyclononen-12-one, oxime there is obtained from 5-ethyl-6,7,8,9,10,11-hexahydro-3-methoxy-5,10-methano-5H-benzocyclononen-12-one (3.5 g.) and 20 ml of hydroxylamine hydrochloride (3.5 g.) of the title product as a brown oil which crystallizes on standing.

I. R. Analysis: 3.2; 6.0 μ.

Crystallization of the crude solid from ethanol water gives the title product, m.p. 114°–116° C.

Analysis for: $C_{17}H_{23}NO_2$: Calculated: C, 74.69; H, 8.48; N, 5.12 Found: C, 75.20; H, 8.93; N, 4.84.

EXAMPLE XXVI

To prepare: 6,7,8,9,10,11-hexahydro-5-benzyl-5,10-methano-5H-benzocyclononen-12-one, oxime treat 6,7,8,9,10,11-hexahydro-5-benzyl-5,10-methano-5H-benzocyclononen-12-one with hydroxylamine hydrochloride as taught in Example XIX, Method C.

To prepare: 5-benzyl-6,7,8,9,10,11-hexahydro-3-methoxy-5,10-methano-5H-benzocyclononen-12-one, oxime treat 5-benzyl-6,7,8,9,10,11-hexahydro-3-methoxy-5,10-methano-5H-benzocyclononen-12-one with hydroxylamine hydrochloride as taught in Example XIX, Method C.

EXAMPLE XXVII 6,7,8,9,10,11-Hexahydro-3-Methoxy-5-Methyl-5,10-Methano-5H-Benzocyclononen-12-Amine A. 6,7,8,9,10,11-Hexahydro-3-methoxy-5-methyl-5,10-methano-5H-benzocyclononen-12-one, oxime (15 g. 0.058 m.) Raney nickel (3 tsps.) ethanol (100 ml.) and concentrated ammonium hydroxide (50 ml.) are shaken with hydrogen at 45 psi and 45° C. The catalyst is removed by filtration and the filtrate concentrated to remove solvent. The residue is distilled under reduced pressure to afford the title product (11 g.), b.p. 140°–142° C. (0.2 mm.) HCl salt, m.p. 298°–299° C.

Analysis for: $C_{16}H_{24}ClNO$: Calculated: C, 68.21; H, 8.58; N, 4.96. Found: C, 67.96; H, 8.63; N, 4.92.

B. Undistilled 6,7,8,9,10,11-hexahydro-3-methoxy-5-methyl-5,10-methanol-5H-benzocyclononen-12-amine (31 g.) in dry ether (200 ml.) is treated with dry hydrogen chloride in ether until the solution is acidic. The precipitated salt is collected, washed with ether and dried to afford a product (32 g.), m.p. 257°–267° C.

This product is dissolved in water (1,000 ml.) and methanol (180 ml.). Addition of concentrated hydrochloric acid (2 ml.), concentration at atmospheric pressure to 500 ml., collection of the precipitate obtained on cooling, followed by washing and drying gives a product (20.0 g.), m.p. 302°–305° C. On the basis of infrared and nuclear magnetic resonance spectra this product is assigned the structure 6,7,8,9,10,11-hexahydro-3-methoxy-5α-methyl-5,10-methano-5H-benzocyclononen-12β-amine, hydrochloride.

Concentration of the mother liquors obtained after isolation of the β-amine product gives a product (2 g.), m.p. 262– 273° C. Further concentration to about 65 ml. clarifying and chilling gives crystals (5.9 g.), m.p. 231°–236° C. which are collected with the aid of additional cold water (50 ml.). Recrystallization is accomplished by dissolving in acetone-methanol (2:1), concentrating to one-half volume then making up to the original volume with acetone. Repetition of the concentration-dilution process three additional times followed by chilling gives a product (4.5 g.), m.p. 237°–240° C.

Analysis for: $C_{16}H_{24}ClNO$: Calculated: C, 68.21; H, 8.58; N, 4.96; Cl, 12.54. Found: C, 68.40; H, 8.72; N, 5.02; Cl, 12.04.

On the basis of infrared and nuclear magnetic resonance spectra this product is assigned the structure 6,7,8,9,10,11-hexahydro-3-methoxy-5α-methyl-5,10-methano-5H-benzocyclononen-12α-amine, hydrochloride.

EXAMPLE XXVIII 6,7,8,9,10,11-Hexahydro-2-Methoxy-5α-Methyl-5,10-Methano-5H-Benzocyclononen-12β-Amine Using a procedure analogous to that described in Example XXVIIA for preparation of 6,7,8,9,10,11-hexahydro-3-methoxy-5-methyl-5,10-methano-5H-benzocyclononen-12-amine, there is obtained from 5.0 g. of 6,7,8,9,10,11-hexahydro-2-methoxy-5-methyl-5,10-methano-5H-benzocyclononen-12-one, oxime 2.8 g. of the title product as its hydrochloride, m.p. 284°–287° C.

Analysis for: $C_{16}H_{24}NOCl$: Calculated: C, 68.21; H, 8.58; N, 4.96. Found: C, 68.09; H, 8.85; N, 4.96.

EXAMPLE XXIX 6,7,8,9,10,11-Hexahydro-1-Methoxy-5α-Methyl-5,10-Methano-5H-Benzocyclononen-12β-Amine Using a procedure analogous to that described in Example XXVIIA for preparation of 6,7,8,9,10,11-hexahydro-3-methoxy-5-methyl-5,10-methano-5H-benzocyclononen-12-amine there is obtained from 10.5 g. of 6,7,8,9,10,11-hexahydro-1-methoxy-5-methyl-5,10-methano-5H-benzocyclononen-12 -one, oxime 7.4 g. of the title product as the hydrochloride, m.p. 308°–309° C.

Analysis for: $C_{16}H_{24}NOCl$: Calculated: C, 68.21; H, 8.58; N, 4.96. Found: C, 68.12; H, 8.60; N, 4.84.

EXAMPLE XXX

5α-Methyl-5,6,7,8,9,10,11,12-Octahydro-5,11-Methano-Benzocyclodecen-13β-Amine

5-Methyl-5,6,7,8,9,10,11,12-octahydro-5,11-methano-5H-benzocyclodecen-13-one, oxime (2.5 g.), Raney nickel (2 g.), ammonium hydroxide (4 ml.) and ethanol (50 ml.) are shaken with hydrogen at 45 psi. After hydrogen uptake ceases (approximately 7 pounds versus 14 pounds theory) the solution is removed from the apparatus, filtered, and concentrated. The residue (pink oil) is combined with fresh Raney nickel, ammonium hydroxide, and ethanol and hydrogenated at 50 psig and 50°–60° C. When completed the solution is worked up as above. The residue, a colorless oil, is converted to the hydrochloride salt, filtered, washed, and dried. The salt is recrystallized from water to give the title compound, as the hydrochloride, 1.15 g., m.p. >335° C.

Analysis for: $C_{16}H_{24}ClN$: Calculated: C, 72.29; H, 9.10; N, 5.27. Found: C, 72.12; H, 9.45; N, 5.28.

EXAMPLE XXXI 6,7,8,9,10,11-Hexahydro-5α-Methyl-5,10-Methano-5H-Benzocyclononen-12β-Amine 6,7,8,9,10,11-Hexahydro-5-methyl-5,10-methano-5H-benzocyclononen-12-one, oxime (2.5 g.), Raney nickel catalyst (6 g.) in 25 ml. of concentrated ammonium hydroxide and 50 ml. of ethanol are shaken with hydrogen at 50 psi and 45° C. After hydrogen uptake stops the catalyst is filtered off, the filtrate concentrated, and the residue converted to the hydrochloride salt (2.8 g.); recrystallization from water gives the title product as its hydrochloride, m.p. >315° C.

Analysis for: $C_{15}N_{22}ClN$: Calculated: C, 71.62; H, 8.81; N, 5.53. Found: C, 71.62; H, 8.81; N, 5.86.

EXAMPLE XXXII

5-Ethyl-6,7,8,9,10,11-Hexahydro-3-Methoxy-5,10-Methano-5H-Benzocyclononen-12-Imine Using a procedure analogous to that described in Example XXVIIA for the preparation of 6,7,8,9,10,11-hexahydro-3-methoxy-5-methyl-5,10-methano-5H-benzocyclononen-12-amine there is obtained from 3.5 g. of 5-ethyl-6,7,8,9,10,11-hexahydro-3-methoxy-5,10-methano-5H-benzocyclononen-12-one, oxime 1.6 g. of the title product, b.p. 150°–160° C. (0.5 mm.).

I. R. Analysis: 6.1 μ.

Addition of ethereal hydrogen chloride to the title product in ether gives the hydrochloride salt, m.p. 252°–255° C. (dec).

Analysis for: $C_{17}H_{24}NOCl$: Calculated: C, 69.48; H, 8.23; N, 4.77. Found: C, 69.25; H, 8.28; H, 4.72.

EXAMPLE XXXIII

5-Ethyl-6,7,8,9,10,11-Hexahydro-3-Methoxy-5,10-Methano-5H-Benzocyclononen-12-Amine A. Using a procedure analogous to that described in Example XXVIIA for the preparation of 6,7,8,9,10,11-hexahydro-3-methoxy-5-methyl-5,10-methano-5H-benzocyclononen-12-amine there is obtained from 5-ethyl-6,7,8,9,10,11-hexahydro-3-methoxy-5,10-methano-5H-benzocyclononen-12-imine (4.0 g.) approximately 3.5 g. of title product which is converted to its solid hydrochloride salt, m.p. 226°–231° C.

On the basis of infrared and nuclear magnetic resonance spectra this product is assigned the structure 5α-ethyl-6,7,8,9,10,11-hexahydro-3-methoxy-5,10-methano-5H-benzocyclononen-12β-amine, hydrochloride.

Analysis for: $C_{17}H_{26}NOCl$: Calculated: C, 69.01; H, 8.86; N, 4.73. Found: C, 68.76; H, 8.94; N, 4.72.

B. Using a procedure analogous to that described in Example XXVIIA for the preparation of 6,7,8,9,10,11-hexahydro-3-methoxy-5-methyl-5,10-methano-5H-benzocyclononen-12-amine, from 5-ethyl-6,7,8,9,10,11-hexahydro-3-methoxy-5,10-methano-5H-benzocyclononen-12-one, oxime there is obtained distilled title product which is shown by gas chromatography-mass spectra data to be approximately a 8 to 1 mixture of epimeric amines. Dissolving 70 g. of this mixture in 1100 ml. of dilute aqueous hydrochloric acid, filtering the solution through diatomaceous earth and allowing it to stand 1 day at room temperature and for 2 days at 10° gives 64 g. of the hydrogen chloride, hydrate salt of 5α-ethyl-6,7,8,9,10,11-hexahydro-3-methoxy-5,10-methano-5H-benzocyclononen-12β-amine with m.p. 253°–256°.

Analysis for: $C_{17}H_{25}NO . NCl . H_2O$: Calculated: C, 65.05; H, 8.99; N, 4.46. Found: C, 65.26; H, 9.01; N, 4.50.

C. The filtrate recovered from B above is made basic with aqueous sodium hydroxide, extracted with ether and the ether extracts dried and concentrated to an oil. This oil is chromatographed on 300 g. of silica gel. Elution with a solution of 3 parts benzene, 1 part chloroform gives 3.0 g. of pure 5α-ethyl-6,7,8,9,10,11-hexahydro-3-methoxy-5,10-methano-5H-benzocyclononen-12α-amine. Conversion of the amine to its hydrogen chloride salt in ether gives a crystalline salt with m.p. 182°–185°.

Analysis for: $C_{17}H_{26}NOCl$; Calculated: C, 69.01; H, 8.86; N, 4.73. Found: C, 68.73; H, 8.91; N, 4.75

EXAMPLE XXXIV 5,6,7,8,9,10-Hexahydro-3-Methoxy-5-Methyl-5,9-Methano-Benzocycloocten-11-Amine A. Using a procedure analogous to that described in Example XXVIIA for the preparation of 6,7,8,9,10,11-hexahydro-3-methoxy-5-methyl-5,10-methano-5H-benzocyclononen-12-amine there is obtained from 5,6,7,8,9,10-hexahydro-3-methoxy-5-methyl-5,9-methano-benzocycloocten-11-one, oxime (4.2 g.), 2.7 g. of the title compound, b.p. 125°–129° C. (0.1 mm.).

A sample is converted to the hydrochloride salt which crystallizes from ethanol:ether, m.p. 262°–264° C.

Analysis for: $C_{15}H_{22}ClNO$: Calculated: C, 67.27; H, 8.28; N, 5.23. Found: C, 67.16; H, 8.48; H, 5.14.

B. Using a procedure analogous to that described in Example XXVIIA for the preparation of 6,7,8,9,10,11-hexahydro-3-methoxy-5-methyl-5,10-methano-5H-benzocyclononen-12-amine, from 5,6,7,8,9,10-hexahydro-3-methoxy-5-methyl-5,10-methano-5H-benzocyclooctene-11-one, oxime, there is obtained distilled title product which is shown by gas chromatography, mass spectral data to be a 3 to 2 mixture of amino epimers. By repeated recrystallization of hydrogen chloride salt of 27 g. of the epimeric amine mixture from ethanol-ether, there is obtained 16.3 g. of product, m.p. 270°–272°, which is assigned the structure 5,6,7,8,9,10-hexahydro-3-methoxy-5α-methyl-5,9-methano-benzocycloocten-11α-amine, hydrochloride.

Analysis for: $C_{15}H_{22}NOCl$: Calculated: C, 67.27; H, 8.28; N, 5.23. Found: C, 67.17; H, 8.48; N, 5.14.

C. Concentration of the combined mother liquors from B gives a residue which is crystallized fromm acetonitrile and then repetitively recrystallized from ethanol ether to give a product, m.p. 300°–302°, which is assigned the structure 5,6,7,8,9,10-hexahydro-3-methoxy-5α-methyl-5,9-methano-benzocycloocten-11β-amine, hydrochloride.

Analysis for: $C_{15}H_{22}$ NOCl: Calculated: C, 67.27; H, 8.28; N, 5.23. Found: C, 67.14; H, 8.24; N, 5.24.

EXAMPLE XXXV

3-Methoxy-5α-Methyl-5,6,7,8,9,10,11,12-Octahydro-5,11-Methano-Benzocyclodecen-13β-Amine Using a procedure analogous to that described in Example XXX for the preparation of 5-methyl-5,6,7,8,9,10,11,12-octahydro-5,11-methano-benzocyclodecen-13-amine there is obtained from 3-methoxy-5-methyl-5,6,7,8,9,10,11,12-octahydro-5,11-methanobenzocyclodecen-13-one, oxime (18.5 g.) Raney nickel (3 tablespoons), 100 ml. of ethanol and 50 ml. of concentrated ammonium hydroxide; after distillation 11.1 g. [b.p. 140°–145° C. (1.2 mm.)] of the title product which is converted to the hydrochloride salt which recrystallizes from water, m.p. 311°–312° C.

Analysis for: $C_{17}H_{26}ClNO$: Calculated: C, 69.13; H, 8.86; N, 4.73. Found: C, 69.17; H, 9.16; N, 4.70.

EXAMPLE XXXVI

To prepare: 6,7,8,9,10,11-hexahydro-5-benzyl-5,10-methano-5H-benzocyclononen-12-amine (hydrochloride salts, m.p. 154°–158° C. reduce 6,7,8,9,10,11-hexahydro-5-benzyl-5,10-methano-5H-benzocyclononen-12-one, oxime as taught in Example XXVII.

To prepare: 5-benzyl-6,7,8,9,10,11-hexahydro-3-methoxy-5,10-methano-5H-benzocyclononen-12-amine (hydrochloride salt, m.p. 152°–156° C.) reduce 5-benzyl-6,7,8,9,10,11-hexahydro-3-methoxy-5,10-methano-5H-benzocyclononen-12-one, oxime as taught in Example XXVII.

EXAMPLE XXXVII 6,7,8,9,10,11-Hexahydro-3-Methoxy-N,5α-Dimethyl-5,10-Methano-5H-Benzocyclononen-12β-Amine 6,7,8,9,10,11-Hexahydro-3-methoxy-5α-methyl-5,10-methano-5H-benzocyclononen-12α-amine, hydrochloride (2.5 g.), saturated aqueous sodium bicarbonate (50 ml.), methylene chloride (50 ml.) and ethylchloroformate (3 ml.) are stirred, at room temperature, for 4 hours. The organic layer is separated, washed successively with aqueous sodium carbonate, hydrogen chloride and sodium chloride, dried and concentrated to give 2.6 g. of oil. This oil is added to a mixture of 1 g. of lithium aluminum hydride in tetrahydrofuran and the resulting mixture is refluxed overnight. Two ml. of water is added and the mixture is filtered. Concentration of the filtrate gives 2.1 g. of oil which is converted to 1.8 g. of hydrogen chloride salt with m.p. 249°–250° after recrystallization from ethanol-ether.

Analysis for: $C_{17}H_{26}NOCl$: Calculated: C, 69.01; H, 8.86; N, 4.73. Found: C, 68.53; H, 9.08; N, 5.13.

EXAMPLE XXXVIII 6,7,8,9,10,11-Hexahydro-3-Methoxy-N,N,5α-Trimethyl-5,10-Methano-5H-Benzocyclononen-12αAmine In a manner analogous to that described in Example XXXVII for the preparation of 6,7,8,9,10,11-hexahydro-3-methoxy-N,5α-dimethyl-5,10-methano-5H-benzocyclononen-12α-amine, from 1.2 g. of 6,7,8,9,10,11-hexahydro-3-methoxy-N,5α-dimethyl-5,10-methano-5H-benzocyclononen-12α-amine there is obtained 0.90 g. of the hydrogen chloride salt of the title product with m.p. 200°–202°.

Analysis for: $C_{18}H_{28}NOCl$: Calculated: C, 69.76; H, 9.11; N, 4.52. Found: C, 69.28; H, 9.12; N, 4.69.

EXAMPLE XXXIX 6,7,8,9,10,11-Hexahydro-3-Methoxy-N,N,5α-Trimethyl-5,10-Methano-5H-Benzocyclononen-12β-Amine In a manner analogous to that described in Example XXXVII for the preparation of 6,7,8,9,10,11-hexahydro-3-methoxy-N,5α-dimethyl-5,10-methano-5H-benzocyclononen-12α-amine, from 1.2 g. of 6,7,8,9,10,11-hexahydro-3-methoxy-N,5α-dimethyl-5,10-methano-5H-benzocyclononen-12α-amine there is obtained 1.0 g. of the hydrogen chloride salt of the title product with m.p. 207°–209°.

Analysis for: $C_{18}H_{28}NOCl$ . 1/4 H O: Calculated: C, 68.79; H, 9.14; N, 4.46. Found: C, 68.83; H, 9.36; N, 4.69.

EXAMPLE XL

5α-Ethyl-6,7,8,9,10,11-Hexahydro-3-Methoxy-N-Methyl-5,10-Methano-5H-Benzocyclononen-12β-Amine In a manner analogous to that described in Example XXXVII for the preparation of 6,7,8,9,10,11-hexahydro-3-methoxy-N,5α-dimethyl-5,10-methano-5H-benzocyclononen-12α-amine, from 8.0 g. of 5α-ethyl-6,7,8,9,10,11-hexahydro-3-methoxy-5,10-methano-5H-benzocyclononen-12β-amine there is obtained 5.5 g. of the hydrogen chloride salt of the title product with m.p. 282°–284° dec. on recrystallization from ethanol-ether.

Analysis for: $C_{18}H_{28}NOCl$: Calculated: C, 69.76; H, 9.11; N, 4.52. Found: C, 69.29; H, 9.22; N, 4.61.

EXAMPLE XLI

5α-Ethyl-6,7,8,9,10,11-Hexahydro-N,N-Dimethyl-3-Methoxy-5,10-Methano-5H-Benzocyclononen-12β-Amine In a manner analogous to that described in Example XXXVII for the preparation of 6,7,8,9,10,11-hexahydro-3-methoxy-N,5α-dimethyl-5,10-methano-5H-benzocyclononen-12α-amine, from 4.0 g. of 5α-ethyl-6,7,8,9,10,11-hexahydro-3-methoxy-N-methyl-5,10-methano-5H-benzocyclononen-12β-amine there is obtained 2.65 g. of the hydrogen chloride salt of the title product with m.p. 162°–165° on recrystallization from ethanol-ether.

Analysis for: $C_{19}H_{30}NOCl$: Calculated: C, 70.56; H, 9.34; N, 4.33. Found: C, 70.14; H, 9.30; N, 4.30.

EXAMPLE XLII

3-Methoxy-N,5α-Dimethyl-5,6,7,8,9,10,11,12-Octahydro-5,11-Methanobenzocyclodecen-13β-Amine In a manner analogous to that described in Example XXXVII for the preparation of 6,7,8,9,10,11-hexahydro-3-methoxy-N,5α-dimethyl-5,10-methano-5H-benzocyclononen-12α-amine, from 8.0 g. of 3-methoxy-5α-methyl-5,6,7,8,9,10,11,12-octahydro-5,11-methanobenzocyclodecen-13β-amine there is obtained 5.5 g. of the hydrogen chloride salt of the title product with m.p. 303°–305° dec. on recrystallization from ethanol-ether.

Analysis for: $C_{18}H_{28}NOCl$: Calculated: C, 69.76; H, 9.11; N, 4.52. Found: C, 69.27; H, 8.99; N, 4.66.

NMR Analysis: N-CH$_3$ signal at δ = 2.48 ppm (free base).

EXAMPLE XLIII

3-Methoxy-N,N,5α-Trimethyl-5,6,7,8,9,10,11,12-Octahydro-5,11-Methanobenzocyclodecen-13β-Amine In a manner analogous to that described in Example XXXVII for the preparation of 6,7,8,9,10,11-hexahydro-3-methoxy-N,5α-dimethyl-5,10-methano-5H-benzocyclononen-12α-amine, from 4.0 g. of 3-methoxy-N,5α-dimethyl-5,6,7,8,9,10,11,12-octahydromethanobenzocyclodecen-13β-amine there is obtained 2.0 g. of the hydrogen chloride salt of the title product with m.p. 195°–198° on recrystallization from ethanol ether.

Analysis for: $C_{19}H_{30}NOCl$ . $H_2O$: Calculated: C, 66.74; H, 9.43; N, 4.10. Found: C, 66.61; H, 9.39; N, 3.96.

EXAMPLE XLIV 5,6,7,8,9,10-Hexahydro-3-Methoxy-N,5α-Dimethyl-5,9-Methanobenzocyclooctene-11β-Amine In a manner analogous to that described in Example XXXVII for the preparation of 6,7,8,9,10,11-hexahydro-3-methoxy-N,5α-dimethyl-5,10-methano-5H-benzocyclononene-12α-amine, from 1.5 g. of 5,6,7,8,9,10-hexahydro-3-methoxy-5α-methyl-5,9-methano-benzocyclooctene-11β-amine there is obtained 1.2 g. of the hydrogen chloride salt of the title product with m.p. 266°–267°.

Analysis for: $C_{16}H_{24}NOCl$: Calculated: C, 68.19; H, 8.58; N, 4.97. Found: C, 67.88; H, 8.88; N, 4.80.

EXAMPLE XLV

5α-Ethyl-6,7,8,9,10,11-Hexahydro-3-Methoxy-N-Methyl-5,10-Methano-5H-Benzocyclononen-12α-Amine In a manner analogous to that described in Example XXXIX for the preparation of 6,7,8,9,10,11-hexahydro-3-methoxy-N,5α-dimethyl-5,10-methano-5H-benzocyclononen-12β-amine, from 1.2 g. of 5α-ethyl-6,7,8,9,10,11-hexahydro-3-methoxy-5,10-methano-5H-benzocyclononen-12α-amine there is obtained 0.90 g. of the hydrogen chloride salt of the title product with m.p. 284°–285° dec. on recrystallization from ethanol-ether.

Analysis for: $C_{18}H_{28}NOCl$ . 1/4 $H_2O$: Calculated: C, 68.77; H, 9.14; N, 4.46. Found: C, 68.69; H, 9.19; N, 4.42.

EXAMPLE XLVI

N-Allyl-6,7,8,9,10,11-Hexahydro-3-Methoxy-5α-Methyl-5,10-Methano-5H-Benzocyclononen-12β-Amine 6,7,8,9,10,11-Hexahydro-3-methoxy-5α-methyl-5,10-methano-5H-benzocyclononen-12β-amine (1.7 g.), allylbromide (0.85 g.), diisopropyl ethyl amine (1.3 g.) and benzene (10 ml.) are heated at reflux for 3 hours. The mixture is cooled, diluted with ether and filtered. The solvents are removed under reduced pressure and the residue distilled to give the title product (1.3 g.), b.p. 144°–146° C. (0.2 mm.). The distilled product is taken up in ether and treated with a slight excess of hydrogen chloride in ether to give the hydrochloride addition salt of the title product (1.3 g.), m.p. 200°–202° C.

Analysis for: $C_{19}H_{28}ClNO$: Calculated C, 70.95; H, 8.74; N, 4.35. Found: C, 70.50; H, 8.77; N, 4.46.

EXAMPLE XLVII

N-Allyl-5,6,7,8,9,10-Hexahydro-3-Methoxy-5α-Methyl-5,9-Methanobenzocycloocten-11α-Amine Using a procedure analogous to that described in Example XXXVI for the preparation of N-allyl-6,7,8,9,10,11-hexahydro-3-methoxy-5α-methoxy-5,10-methano-5H-benzocyclononen-12β-amine there is obtained from 5,6,7,8,9,10-hexahydro-3-methoxy-5α-methyl-5,9-methano-benzocycloocten-11-amine (1.4 g.), 1.3 g. of the title product, b.p. 148°–153° C. (0.3 mm.). A sample is converted to the hydrochloride.

Analysis for: $C_{18}H_{26}ClNO$: Calculated: C, 70.22; H, 8.51; N, 4.55. Found: C, 69.75; H, 8.73; N, 4.47.

EXAMPLE XLVIII 6,7,8,9,10,11-Hexahydro-3-Methoxy-5α-Methyl-N-Phenethyl-5,10-Methano-5H-Benzocyclononen-12β-Amine A mixture of 6,7,8,9,10,11-hexahydro-3-methoxy-5α-methyl-5,10-methano-5H-benzocyclononen-12β-amine (2.4 g.), phenethyl bromide (3 g.), and diisopropyl ethylamine (1.3 g.) in xylene (20 ml.) is heated at reflux for 18 hours. After cooling ether is added (100 ml.) and the solid material is filtered off and washed with ether. The combined filtrate is extracted with dilute hydrochloric acid. The solid residue is dissolved in warm water, and added to the acid extract. The solution is basified with 10% sodium hydroxide and the oily layer which separates is taken into ether. After removal of the solvent the residue is distilled and the fraction boiling at 190°–198° (0.2 mm.) is collected. This is converted to the hydrochloride salt in ether which is recrystallized from i-propanol to give the title product as its hydrochloride salt, m.p. 243°–245° C.

Analysis for: $C_{24}H_{32}ClNO$: Calculated: C, 74.80; H, 8.36; N, 3.63. Found: C, 74.55; H, 8.74; N, 3.55.

EXAMPLE XLIX 6,7,8,9,10,11-Hexahydro-3-Methoxy-5α-Methyl-N-(3-Methyl-2-Butenyl)-5,10-Methano-5H-Benzocyclononen-12β-Amine 6,7,8,9,10,11-Hexahydro-3-methoxy-5-methyl-5,10-methano-5H-benzocyclononen-12-amine (4.5 g.), 3,3-dimethylallylbromide (4.5 g.), diisopropyl ethylamine (5.75 g.) and xylene (60 ml.) are heated at reflux for 4 hours. The mixture is cooled, diluted with ether and filtered. The solvent is removed under vacuum and the residue is distilled to give the title product (1.2 g.), b.p. 166°–170° C. (0.2 mm.). A sample is converted to the hydrochloride and recrystallized from ethanol, m.p. 295°–298° C.

Analysis for: $C_{17}H_{26}ClNO$: Calculated: C, 69.01; H, 8.86; N, 4.73. Found: C, 68.90; H, 8.92; N, 4.83.

EXAMPLE L 5,6,7,8,9,10-Hexahydro-3-Methoxy-5α-Methyl-N-(3-Methyl-2-Butenyl)-5,9-Methano-Benzocycloocten-11β-Amine 5,6,7,8,9,10-Hexahydro-3-methoxy-5α-methyl-5,9-methanobenzocycloocten-11β-amine (1.4 g.), diisopropylethylamine (1.3 g.), and 1-chloro-3-methyl-2-butene (0.7 g.) are refluxed 7 hours in xylene. The reaction is cooled to room temperature, filtered and the filtrate extracted with 2N hydrochloride acid. The aqueous extract is basified and extracted with ether. The ether extract is then washed with water, dried over sodium sulfate, concentrated in vacuo, and the residue distilled under reduced pressure to give the title product (1.5 g.), b.p. 150°–155° C. (0.5 mm.). Treatment of the product in ether with hydrogen chloride gives the hydrochloride, m.p. 166°–169° C.

Analysis for: $C_{20}H_{30}ClNO$: Calculated: C, 71.51; H, 9.00; H, 4.17. Found: C, 71.58; H, 9.09; H, 4.20.

EXAMPLE LI

12β-Amino-6,7,8,9,10,11-Hexahydro-5α-Methyl-5,10-Methano-5H-Benzocyclononen-3Ol

A solution of 6,7,8,9,10,11-hexahydro-3-methoxy-5α-methyl-5,10 -methano-5H-benzocyclononen-12β-amine (1.19 g.) in 48% hydrobromic acid (15 ml.) is refluxed 30 minutes under nitrogen. The mixture is cooled, diluted with water (50 ml.), filtered and evaporated to dryness under reduced pressure. The residue is dissolved in ethanol (50 ml.) and again taken to dryness. Redissolving in ethanol (25 ml.), addition of ether (50 ml.), and standing in the cold gives crystals which are recrystallized from i-propanol to give the hydrobromide salt of the title product as the i-propanolate (0.72 g.), m.p. 246°–248° C.

Analysis for: $C_{18}H_{30}BrNO_2$; Calculated: C, 58.10; H, 8.07; N, 3.76. Found: C, 57.52; H, 8.71; N, 3.69.

EXAMPLE LII

12β-Amino-6,7,8,9,10,11-Hexahydro-5α-Methyl-5,10-Methano-5H-Benzocyclononen-2-Ol Using a procedure analogous to that described in Example LI for the preparation of 12β-amino-6,7,8,9,10,11-hexahydro-5α-methyl-5,10-methano-5H-benzocyclononen-3-ol there is obtained from approximately 1.2 g. of 6,7,8,9,10,11-hexahydro-2-methoxy-5-methyl-5,10-methano-5H-benzocyclononen-12-amine, 1.2 g. of the hydrogen bromide salt of the title product, m.p. 299°–303° C.

Analysis for: $C_{15}H_{22}BrNO$: Calculated: C, 57.69; H, 7.10; N, 4.49. Found: C, 57.53; H, 7.13; N, 4.44.

EXAMPLE LIII

13β-Amino-5α-Methyl-5,6,7,8,9,10,11,12-Octahydro-5,11-Methano-Benzocyclodecen-3-Ol 3-Methoxy-5α-methyl-5,6,7,8,9,10,11,12-octahydro-5,11-methano-benzocyclodecen-13β-amine (3g.) is refluxed in 60 ml. 48% aqueous hydrobromic acid for one hour. The mixture is poured into ice (100 g.) and stirred. The precipitate is then filtered off, washed with cold water, then with ether and dried. Recrystallization from water (after treating with activated charcoal) gives the title product, 1.85 g., m.p. 269°–270° C.

Analysis for: $C_{16}H_{24}BrNO \cdot 1/2H_2O$: Calculated: C, 57.18; H, 7.52; N, 3.97. Found: C, 57.22; H, 7.61; N, 4.14.

EXAMPLE LIV

12β-Amino-6,7,8,9,10,11-Hexahydro-5α-Methyl-5,10-Methano-5H-Benzocyclononen-1-Ol Using a procedure analogous to that described in Example LI for the preparation of 12β-amino-6,7,8,9,10,11-hexahydro-5α-methyl-5,10-methano-5H-benzocyclononen-3-ol, there is obtained from approximately 1.6 g. of 6,7,8,9,10,11-hexahydro-1-methoxy-5-methyl-5,10-methano-5H-benzocyclononen-12-amine, 1.75 g. of the hydrogen bromide salt of the title product, m.p. 245°–250° C.

Analysis for: $C_{15}H_{22}BrNO$: Calculated: C, 57.69; H, 7.10; N, 4.49. Found: C, 57.40; H, 7.02; N, 4.47.

EXAMPLE LV

12β-Amino-6,7,8,9,10,11-Hexahydro-5α-Ethyl-5,10-Methano-5H-Benzocyclononen-3-Ol

A mixture of 5α-ethyl-6,7,8,9,10,11-hexahydro-5,10-methano-3-methoxy-5H-benzocyclononen-12β-amine (2.0 g.) and 75 ml. of 48% hydrobromic acid is refluxed for one-half hour, then concentrated to a viscous oil. The oil is dissolved in water and treated with concentrated aqueous ammonia. Filtration gives 1.7 g. of a crude product, m.p. 170°–191° C. Recrystallization from ethyl acetate gives the title product, m.p. 202°–204° C.

Analysis for: $C_{16}H_{23}NO$: Calculated: C, 78.32; H, 9.45; N, 5.71. Found: C, 77.93; H, 9.68; N, 5.88.

EXAMPLE LVI

11α-(Dimethylamino)-5,6,7,8,9,10-Hexahydro-5α-Methyl-5,9-Methano-Benzocycloocten-3-Ol 5,6,7,8,9,10-Hexahydro-3-methoxy-N,N,5α-trimethyl-5,9-methano-benzocycloocten-11α-amine (1.2 g.) is refluxed for one hour under a dry nitrogen atmosphere in 13 ml. of aqueous 48% hydrobromic acid. Concentration of the solution affords a residue which on recrystallization from ethanol-ether gives the title product as its hydrobromic acid salt, m.p. 268°–271° C.

Analysis for: $C_{16}H_{24}NOBr$: Calculated: C, 58.89; N, 7.41; N, 4.29. Found: C, 58.80; N, 7.52; N, 4.22.

EXAMPLE LVII

11α-Amino-5,6,7,8,9,10-Hexahydro-5α-Methyl-5,9-Methanobenzocycloocten-3-Ol

In a manner analogous to that described in Example LI for the preparation of 12β-amino-6,7,8,9,10,11-hexahydro-5α-methyl-5,10-methano-5H-benzocyclononen-3-ol, from 2.0 g. of 5,6,7,8,9,10-hexahydro-3-methoxy-5α-methyl-5,9-methanobenzocyclooctene-11α-amine there is obtained 2.3 g. of the hydrogen bromide, ethanolate salt of the title product with m.p. 277°–280° on recrystallization from ethanol-ether.

Analysis for: $C_{14}H_{20}NOBr \cdot 1/2\ C_2H_5OH$: Calculated: C, 56.07; H, 7.22; H, 4.36. Found: C, 55.86; H, 7.37; N, 4.10.

EXAMPLE LVIII

11β-Amino-5,6,7,8,9,10-Hexahydro-5α-Methyl-5,9-Methanobenzocycloocten-3-Ol

In a manner analogous to that described in Example LI for the preparation of 12β-amino-6,7,8,9,10,11-hexahydro-5α-methyl-5,10-methano-5H-benzocyclononen-3-ol, from 1.25 g. of 5,6,7,8,9,10-hexahydro-3-methoxy-5α-methyl-5,9-methanobenzocyclooctene-11β-amine there is obtained 1.05 g. of the hydrogen bromide salt of the title product with m.p. 305°–310° dec. on recrystallization from ethanol-ether.

Analysis for: $C_{14}H_{20}NOBr$: Calculated: C, 56.38; H, 6.76; N, 4.70. Found: C, 56.01; H, 6.79; N, 4.63.

EXAMPLE LIX

12α-Amino-6,7,8,9,10,11-Hexahydro-5α-Methyl-5,10-Methano-5H-Benzocyclononen-3Ol

In a manner analogous to that described in Example LI for the preparation of 12β-amino-6,7,8,9,10,11-hexahydro-5α-methyl-5,10-methano-5H-benzocyclononen-3-ol, from 1.2 g. of 6,7,8,9,10,11-hexahydro-3-methoxy-5α-methyl-5,10-methano-5H-benzocyclononen-12α-amine there is obtained 1.1 g. of the hydrogen bromide salt of the title compound with m.p. 130°–134° on recrystallization from acetonitrile.

Analysis for: $C_{15}H_{21}NO \cdot HBr \cdot 1/4\ CH_3CN$: Calculated: C, 57.72; H, 7.11; N, 5.43. Found: C, 57.47; H, 7.00; N, 5.57.

EXAMPLE LX

12α-Amino-6,7,8,9,10,11-Hexahydro-5α-Ethyl-5,10-Methano-5H-Benzocyclononen-3-Ol

In a manner analogous to that described in Example LI for the preparation of 12β-amino-6,7,8,9,10,11-hexahydro-5α-methyl-5,10-methano-5H-benzocyclononen-3-ol, from 1.0 g. of 5α-ethyl-6,7,8,9,10,11-hexahydro-3-methoxy-5,10-methano-5H-benzocyclononen-12α-amine, there is obtained 0.72 g. of the hydrogen bromide salt of the title product m.p. 266°–270° on recrystallization from ethanol-ether.

Analysis for: $C_{16}H_{24}NOBr$: Calculated: C, 58.89; H, 7.41; N, 4.29. Found: C, 58.50; H, 7.47; N, 4.10

EXAMPLE LXI 6,7,8,9,10,11-Hexahydro-3-Methoxy-N,5α-Dimethyl-5,10-Methano-5H-Benzocyclononen-12β-Amine 6,7,8,9,10,11-Hexahydro-3-methoxy-5-methyl-5,10-methano-5H-benzocyclononen-12-one (3 g.), calcium oxide (2 g.), and liquid methyl amine (10 ml.) are heated in a sealed vessel at 180°–190° C. for 18 hours. After cooling the mixture is diluted with ether and filtered to separate the hydrated calcium oxide. The filtrate is concentrated to an oil which is taken up in ethanol and shaken with hydrogen at 45 psi in the presence of platinum dioxide catalyst. The catalyst is removed by filtration, rinsed thoroughly with ethanol and combined filtrate is concentrated in vacuo. The residue was distilled under reduced pressure to give the title product (1.8 g.), b.p. 138°–144° C. (0.2 mm.). For analytical purposes a sample is converted to the hydrochloride which crystallizes from ethanol, m.p. 295°–298° C.

Analysis for: $C_{17}H_{22}ClNO$: Calculated: C, 69.01; H, 8.86; N, 4.73. Found: C, 68.90; H, 8.92; H, 4.83.

EXAMPLE LXII 5,6,7,8,9,10-Hexahydro-3-Methoxy-5α-Methyl-N-Phenethyl-5,9-Methano-Benzocycloocten-11α-Amine Using a procedure analogous to that described in Example LXI for the preparation of N,5α-dimethyl-6,7,8,9,10,11-hexahydro-3-methoxy-5,10-methano-5H-benzocyclononen-12β-amine there is obtained from 5,6,7,8,9,10-hexahydro-3-methoxy-5-methyl-5,9-methanobenzocycloocten-11-one (2.3 g.) 1.80 g. of the title product, b.p. 170°–200° C. (0.5 mm.). A sample is converted to the hydrochloride salt.

Analysis for: $C_{23}H_{30}ClNO$: Calculated, C, 74.27; H, 8.12; N, 3.77. Found: C, 74.23; H, 8.29; N, 3.59.

EXAMPLE LXIII 5,6,7,8,9,10-Hexahydro-3-Methoxy-N,5α-Dimethyl-5,9-Methano-Benzocycloocten-11α-Amine Using a procedure analogous to that described in Example LXI for the preparation of 6,7,8,9,10,11-hexahydro-3-methoxy-N,5α-dimethyl-5,10-methano-5H-benzocyclononen-12β-amine there is obtained from 5,6,7,8,9,10-hexahydro-3-methoxy-5-methyl-5,9-methano-benzocycloocten-11-one (9.5 g.), 5.4 g. of the title product as the hydrochloride salt, m.p. 232°–236° C.

Analysis for: $C_{16}H_{24}ClNO$: Calculated: C, 68.19; H, 8.58; N, 4.97. Found: C, 67.83; H, 8.45; N, 4.91.

EXAMPLE LXIV

N-Allyl-N,5α-Dimethyl-5,6,7,8,9,10-Hexahydro-3-Methoxy-5,9-Methano-Benzocycloocten-11α-Amine N-Allyl-5,6,7,8,9,10-hexahydro-3-methoxy-5α-methyl-5,9-methano-benzocycloocten-11α-amine (3 g.), ethyl-chloroformate (3 ml.), saturated aqueous sodium bicarbonate (50 ml.) and methylene chloride (25 ml.) are stirred vigorously overnight at room temperature. The layers are then separated, the methylene chloride washed with 2N hydrochloric acid, dried over potassium carbonate and concentrated in vacuo. The residue obtained (3.3 g.) is dissolved in tetrahydrofuran (100 ml.), stirred and refluxed under nitrogen with lithium aluminum hydride (1 g.) for 20 hours. The mixture is cooled, water (1.5 ml.) added to destroy excess hydride, and aluminum salts removed by filtration. The filtrate is dried and concentrated in vacuo and the residue distilled to give the title product (1.4 g.), b.p. 130°–135° C. (0.5 mm.). A portion is dissolved in ether, treated with hydrogen chloride, the crystals recovered by filtration and recrystallized from ethyl acetate to give a hydrochloride salt, m.p. 164°–166° C.

Analysis for: $C_{19}H_{28}ClNO$: Calculated: C, 70.89; H, 8.77; N, 4.35. Found: C, 71.06; H, 9.07; N, 4.53.

EXAMPLE LXV 5,6,7,8,9,10-Hexahydro-3-Methoxy-N,N,5-Trimethyl-5,9-Methano-Benzocyloocten-11-Amine Using a procedure analogous to that described in Example LXIV for the preparation of N-allyl-N,5-dimethyl-5,6,7,8,9,10-hexahydro-3-methoxy-5,9-methano-benzocycloocten-11-amine there is obtained from N,5-dimethyl-5,6,7,8,9,10-hexahydro-3-methoxy-5,9-methano-benzocycloocten-11-amine (11.1 g.), 8.1 g. of the title product, b.p. 125°–230° C. (0.3 mm.). The product in solution in ether is converted by treatment with hydrogen chloride to a crystalline hydrochloride salt. Recrystallization from ethanol-ether gives a product, A, m.p. 180°–190° which is recrystallized from ethanol-ether to give a product having needle-shaped crystals, m.p. 225°–226° C.

Analysis for: $C_{17}H_{26}ClNO$: Calculated: C, 69.01; H, 8.86; N, 4.74. Found: C, 68.89; H, 8.92; N, 4.70.

On the basis of infrared and nuclear magnetic resonance spectra this product is assigned the structure 5,6,7,8,9,10-hexahydro-3-methoxy-N,N,5α-trimethyl-5,9-methano-benzocyclooctane-11β-amine, hydrochloride.

From the mother liquors remaining after crystallization of product A, after concentration, is obtained a second product, m.p. 218°–223° C., recrystallization from ethanol-ether gives a product having hexagonal crystals, m.p. 221°–223° C.

Analysis for: $C_{17}H_{26}ClNO$: Calculated: C, 69.01; H, 8.86; N, 4.74. Found: C, 68.89; H, 8.64; N, 4.74.

On the basis of infrared and nuclear magnetic resonance spectra this product is assigned the structure 5,6,7,8,9,10-hexahydro-3-methoxy-N,N,5α-trimethyl-5,9-methano-benzocyclooctane-11α-amine, hydrochloride.

EXAMPLE LXVI

N,5α-Dimethyl-N-Phenethyl-5,6,7,8,9,10-Hexahydro-3-Methoxy-5,9-Methano-Benzocycloocten-11α-Amine Using a procedure analogous to that described in Example LXIV for the preparation of N-allyl-N,5-dimethyl-5,6,7,8,9,10-hexahydro-3-methoxy-5,9-methano-benzocycloocten-11-amine there is obtained from 5,6,7,8,9,10-hexahydro-3-methoxy-5-methyl-N-phenethyl-5,9-methano-benzocycloocten-11-amine (3.8 g.) 3.1 g. of the title product, b.p. 185°–190° C. (0.3 mm.). Treatment of a portion of the product in acetone with one equivalent of fumaric acid gives the fumarate salt which is recrystallized from acetone as a hydrate, m.p. 149°–151° C.

Analysis for: $C_{28}H_{35}NO_5 \cdot \frac{1}{4}H_2O$: Calculated: C, 71.53; H, 7.61; N, 2.98. Found: C, 71.58; H, 7.73; N, 2.98.

EXAMPLE LXVII

N,5α-Dimethyl-5,6,7,8,9,10-Hexahydro-3-Methoxy-N-(3-Methyl-2-Butenyl)-5,9-Methano-Benzocycloocten-11α-Amine Using a procedure analogous to that described in Example LXIV for the preparation of N-allyl-N,5-dimethyl-5,6,7,8,9,10-hexahydro-3-methoxy-5,9-methanobenzocycloocten-11-amine, there is obtained from 5,6,7,8,9,10-hexahydro-3-methoxy-5-methyl-N-(3-methyl-2-butenyl)-5,9-methano-benzocycloocten-11-amine (3.6 g.) 2.6 g. of the title product, b.p. 150°–155° C. (0.4 mm.). Treatment of a portion of the product in acetone with fumaric acid gives the crystalline fumaric acid salt as a hydrate, m.p. 136°–138° C.

Analysis for: $C_{25}H_{35}NO_5 \cdot \frac{1}{4}H_2O$: Calculated: C, 69.19; H, 8.24; N, 3.22. Found: C, 69.20; H, 8.11; N, 3.32.

EXAMPLE LXVIII

N,5α-Dimethyl-6,7,8,9,10,11-Hexahydro-3-Methoxy-N-(3-Methyl-2-Butenyl)-5,10-Methano-5H-Benzocyclononen-12β-Amine 6,7,8,9,10,11-Hexahydro-3-methoxy-5-methyl-N-(3-methyl-2-butenyl)-5,10-methano-5H-benzocyclononen-12-amine (3.5 g.), ethyl chloroformate (6 g.), saturated aqueous sodium bicarbonate (100 ml.) and methylenedichloride (50 ml.) are stirred vigorously at room temperature for 24 hours. The layers are then separated and the organic layer is washed with 2N hydrochloric acid, dried over potassium carbonate and concentrated in vacuo. The residue (3 g.) is dissolved in tetrahydrofuran (50 ml.) and added to a suspension of lithium aluminum hydride in tetrahydrofuran (50 ml.) stirred and heated to reflux for 18 hours. After cooling, water (4.5 ml.) is added and the reaction mixture is stirred 30 minutes and filtered. The filtrate is dried over anhydrous sodium sulfate and concentrated. The residue (2 g.) is treated with fumaric acid in acetone to give the fumarate salt of the title product as the hemihydrate (1.8 g.), m.p. 108°–110° C.

Analysis for: $C_{26}H_{37}NO_2 \cdot \frac{1}{2} H_2O$: Calculated: C, 69.02; H, 8.47; N, 3.08. Found: C, 68.82; H, 8.54; N, 2.94.

EXAMPLE LXIX

12β-Amino-6,7,8,9,10,11-Hexahydro-5α-Methyl-5,10-Methano-5H-Benzocyclononen-3Ol, Acetate A. A mixture of 12-amino-6,7,8,9,10,11-hexahydro-5-methyl-5,10-methano-5H-benzocyclononen-3-ol (15.0 g.), carbobenzyloxy chloride (11.6 g.) and 100 ml. of saturated aqueous sodium bicarbonate are stirred for 30 minutes. Methylene chloride (100 ml.) is added and the mixture stirred for 1 hour. The organic layer is separated, dried and concentrated. The residue is triturated with ethyl acetate and pentane, then filtered to give 24 g. of crude product. Recrystallization from ethyl acetate-cyclohexane gives 18.3 g. of carbobenzyloxylated amine with m.p. 103°–110°.

B. A solution of the carbobenzyloxylated amine (5.0 g.) of part A above, acetic anhydride (10 ml.) and pyridine (50 ml.) is allowed to stand overnight. The solution is diluted with water and extracted with ether. The ether extracts are washed with 2% aqueous hydrochloric acid, dried and concentrated to give 5.1 g. of o-acetylated product shown to be pure by thin layer chromatography.

C. A solution of the o-acetyl product of part B above (2.5 g.) and hydrogen chloride gas (0.75 g.) in tetrahydrofuran (50 ml.) is hydrogenated in a Parr apparatus over 250 mg. of 10% palladium on carbon under 40 lbs. of hydrogen pressure for 90 minutes. The catalyst is filtered and concentration of the filtrate gives 2.2 g. of title product as a viscous glass. Crystallization of the glassy product from tetrahydrofuran-ether gives crystalline 12β-amino-6,7,8,9,10,11-hexahydro-5α-methyl- 5,10-methano-5H-benzocyclononen-3-ol, acetate, hydrochloride with m.p. 268° dec.

Analysis for: $C_{17}H_{24}NO_2Cl$: Calculated: C, 65.90; H, 7.81; N, 4.52. Found: C, 65.38; H, 7.82; H, 4.48.

EXAMPLE LXX

12β-Amino-6,7,8,9,10,11-Hexahydro-5α-Methyl-5,10-Methano-5H-Benzocyclononen-3Ol, Cyclopropane Carboxylate A. A solution of 2.0 g. of the carbobenzyloxylated amine, described in Example LXIX part A, and 2.0 ml. of cyclopropane carboxoyl chloride in 10 ml. of pyridine is allowed to stand overnight. The solution is diluted with water and extracted with ether. The ether extracts are washed with 2% aqueous hydrochloric acid, dried and concentrated to an oil. The oil is chromatographed on 70 g. of activity III Woelm alumina. Elution with ether gives 1.5 g. of oil which is crystallized from ethyl acetate hexane to give 1.2 g. of O-cyclopropane carboxylate derivative with m.p. 104°–109°.

B. In a manner analogous to that described in Example LXIX, part C, for the preparation of 12-amino-6,7,8,9,10,11-hexahydro-5-methyl-5,10-methano-5H-benzocyclononen-3-ol, acetate, from 1.0 g. of the O-cyclopropane carboxylate derivative of part A of above there is obtained 0.45 g. of the hydrogen chloride salt of the title product with m.p. 255°–57° dec. on crystallization from tetrahydrofuran-ether.

Analysis for: $C_{19}H_{26}NO_2Cl \cdot \frac{1}{4}H_2O$: Calculated: C, 67.04; H, 7.85; N, 4.12. Found: C, 66.79; H, 7.68; N, 4.14.

EXAMPLE LXXI

Resolution of 5α-Ethyl-6,7,8,9,10,11-Hexahydro-3-Methoxy-5,10-Methano-5H-Benzocyclononen-12β-Amine A solution of 5α-ethyl-6,7,8,9,10,11-hexahydro-3-methoxy-5,10-methano-5H-benzocyclononen-12β-amine (64.6 g., 0.249 mole) in 300 ml. of methanol is added to a solution of 41.5 g. (0.275 mole) of l-tartaric acid in 1400 ml. of methanol. The resulting solution is warmed, filtered and diluted to 2000 ml. and allowed to stand for 3 days. Filtration then gives 36.1 g. of salt with m.p. 200°–203° dec. and $[\alpha]_D = -27°$ (1% in dimethyl formamide). Recrystallization of the salt from methanol gives 29.1 g. with m.p. 212°–214° and $[\alpha]_D = -32.8°$. This salt is converted to the free base by treating it with aqueous sodium hydroxide extracting the aqueous mixture with ether and drying the ether extracts over anhydroux magnesium sulfate. On removal of the drying agent and the ether solvent 17.6 g. of resolved base is obtained. This is converted to its hydrogen chloride, hydrate salt which has a m.p. 115°–119° dec. and $[\alpha]_D = -44.1°$ (2% in methanol).

To obtain the opposite rotating isomer, the mother liquors from the first crystallizations of above are concentrated, the residue treated with aqueous sodium hydroxide and extracted with ether. On drying the ether extracts over anhydrous magnesium sulfate and concentrating the extracts, 41.5 g. of base is obtained. This is dissolved in 500 ml. of methanol and the solution is added to a solution of 26.4 g. of d-tartaric acid in 1000 ml. of methanol. This solution is diluted to 1600 ml. and allowed to stand for 5 days. Filtration gives 36.7 g. of salt with m.p. 205°–209° dec. and $[\alpha]_D = +30.3°$ (1% in dimethylformamide). Recrystallization of this salt from methanol gives 30.0 g. of salt with m.p. 209°–211°dec. and $[\alpha]_D = +31.9°$. Conversion of this salt to free base by the same procedure as for the minus rotating isomer described above gives 16.8 g. of base. This is converted to its hydrogen chloride hydrate salt which has m.p. 115°–119° dec. and $[\alpha]_D = +44.5°$ (2% in methanol).

EXAMPLE LXXII

Preparation of Plus and Minus Rotating Isomers of 12β-Amino-6,7,8,9,10,11-Hexahydro-5α-Ethyl-5,10-Methano-5H-Benzocyclononen-3-Ol A. A mixture of optically pure minus rotating 5α-ethyl-6,7,8,9,10,11-hexahydro-3-methoxy-5,10-methano-5H-benzocyclononen-12β-amine (9.5 g.) and 80 ml. of 48% aqueous hydrobromic acid are heated at the reflux temperature under a dry nitrogen atmosphere for 30 minutes. The resulting solution is concentrated to 40 ml., diluted to 150 ml. with water and basified with concentrated aqueous ammonia. After allowing to stand one hour, the mixture is filtered to give 8.9 g. of product with m.p. 185°–191°. Recrystallization of the product from ethyl acetate gives 7.5 g. with m.p. 194°–196° and $[\alpha]_D = -51.3°$ (2% in methanol).

B. When optically pure plus rotating 5α-ethyl-6,7,8,9,10,11-hexahydro-3-methoxy-5,10-methano-5H-benzocyclononen-12β-amine (9.3 g.) is treated with aqueous 48% hydrobromic acid as in A, there is obtained 9.3 g. of crude product with m.p. 178°–190°. Recrystallization of this from ethyl acetate gives 7.0 g. of product with m.p. 194°–196° and $[\alpha]_D = +52.0°$ (2% in methanol).

EXAMPLE LXXIII

When the following compounds are administered to rats by the routes indicated, for evaluation of analgesic potential by the procedure described hereinabove, they exhibit the effective dose-50 values tabulated.

| Compound | Mode of Administration | Effective dose-50 (mg/kg body weight) |
| --- | --- | --- |
| 6,7,8,9,10,11-hexahydro-3-methoxy-5α-methyl-5,10-methano-5H-benzocyclononen-12β-amine | intraperitoneal<br>oral | 25<br>30 |
| 12β-amino-6,7,8,9,10,11-hexahydro-5α-methyl-5,10-methano-5H-benzocyclononen-3-ol | intraperitoneal<br>intramuscular<br>oral | 7.5<br>1.8<br>23 |
| 5α-ethyl-6,7,8,9,10,11-hexahydro-3-methoxy-5,10-methano-5H-benzocyclononen-12β-amine | intraperitoneal<br>intramuscular<br>oral | 3.5<br>13.5<br>11 |
| 12β-amino-6,7,8,9,10,11-hexahydro-5α-ethyl-5,10- | intraperitoneal<br>intramuscular | 3.5<br>0.25 |

| Compound | Mode of Administration | Effective dose-50 (mg/kg body weight) |
| --- | --- | --- |
| methano-5H-benzocyclononen-3-ol | oral | 12 |
| 3-methoxy-5α-methyl-5,6,7,8,9,10,11,12-octahydro-5,11-methano-benzocyclodecen-13β-amine | intraperitoneal<br>intramuscular<br>oral | 4.5<br>15<br>9 |
| 13β-amino-5α-methyl-5,6,7,8,9,10,11,12-octahydro-5,11-methano-benzocyclodecen-3-ol | intraperitoneal<br>intramuscular<br>oral | 1.1<br>0.47<br>9 |
| (-)-13β-amino-5,6,7,8,9,10,11,12-octahydro-5α-methyl-5,11-methano-benzocyclodecen-3-ol | intraperitoneal<br>intramuscular<br>oral | 0.78<br>0.09<br>2.0 |

EXAMPLE LXXIV

1-Ethoxycarbonyl-2-Indanone

To a stirred mixture of sodium hydride (126 g. of a 57% suspension in nujol), 2000 ml. of benzene and 2 ml. of ethanol heated at its reflux temperature under dry nitrogen is added dropwise the diethyl ester of o-phenylene-diacetic acid (335.6 g.) in 700 ml. of benzene. The mixture is refluxed 1.5 hours, poured into water and extracted with ether. The ether extracts are dried and concentrated to give an oil which is crystallized from ethanol-water to give 220 g. of the title product with m.p. 58°–61°.

EXAMPLE LXXV 1-(3-Bromopropyl)-1-Ethoxycarbonyl-2-Indanone

To a stirred solution of 1,3-dibromopropane (175 ml.) and ethanol (250 ml.) is added dropwise a solution of 1-ethoxy-carbonyl-2-indanone (51 g.) and sodium hydroxide (10 g.) in 500 ml. of ethanol and 200 ml. of water. The solution is refluxed for 5 hours and cooled. The bottom layer is separated and the upper layer is diluted with water and extracted with two 100 ml. portions of carbon tetrachloride. The combined lower layers were washed with 5% aqueous sodium hydroxide and water then concentrated and distilled to give, after a small forecut, the title product (40.3 g.) with b.p. 155°–165° at 0.5 mm.

EXAMPLE LXXVI

1-Ethoxycarbonyl-1,3-Propano-2-Indanone

To a stirred mixture of benzene (400 ml.) and sodium hydride (5.3 g. of a 57% suspension in nujol), which is free of nujol, is added dropwise, under dry nitrogen, 1-(3-bromopropyl)-1-ethoxycarbonyl-2-indanone (39.3 g.) in 100 ml. of benzene. The mixture is stirred at room temperature for 18 hours. Water is added and the organic layer is separated, washed with aqueous sodium chloride, dried, concentrated and distilled to give after a small forecut, 20.5 g. of the title product with b.p. 130°–145° at 0.5 mm.

EXAMPLE LXXVII

1-Ethoxycarbonyl-1,3-Propano-2-Indanone, Oxime

A mixture of hydroxylamine hydrochloride (2.1 g.), sodium acetate (2.5 g.), water (10 ml.), ethanol (40 ml.) and 1-ethoxycarbonyl-1,3-propano-2-indanone (2.5 g.) is heated quickly to its reflux temperature and kept at reflux for 5 minutes. The mixture is diluted with water and extracted with ether. The ether extracts are dried and concentrated to give an oil. Chromatography of the oil on activity III alumina gives, with elution with benzene, 2.0 g. of oil which, when triturated with ethyl-acetate-heptane and filtered, gives 1.20 g. of the title product with m.p. 118°–119°.

EXAMPLE LXXVIII

10-Amino-6,7,8,9-Tetrahydro-5,9-Methano-5H-Benzocycloheptene-5-Methanol

A mixture of 1-ethoxycarbonyl-1,3-propano-2-indanone oxime (1.9 g.) and lithium aluminum hydride (1.6 g.) and 100 ml. of tetrahydrofuran is heated at its reflux temperature under dry nitrogen for 40 hours and allowed to stand for 3 days at room temperature. A few ml. of concentrated aqueous ammonia is added and after 15 minutes stirring the mixture is filtered. The filter cake is washed twice with isopropanol containing a little ammonia. The combined filtrates are concentrated to give 1.6 g. of oil which when treated with hydrogen chloride in ether and ethanol gives 1.2 g. of crystalline hydrochloride salt of the title product with m.p. 217°–220°.

Analysis for: $C_{13}H_{18}NOCl$: Calculated: C, 65.12; H, 7.57; N, 5.84. Found: C, 64.99; H, 7.80; N, 5.73.

EXAMPLE LXXIX

5-Methyl-6,7,8,9-Tetrahydro-5,9-Methano-5H-Benzocyclohept-10-Amine

To a cold (5°) mixture of pyridine (50 ml.) and 10-amino-6,7,8,9-tetrahydro-5,9-methano-5H-benzocycloheptane-5-methanol, hydrochloride (5.1 g.) is added, in portions, 8.0 g. of o-toluenesulfonyl chloride in 20 ml. of pyridine. After keeping on ice for 3 hours, 8.0 g. of p-toluenesulfonyl chloride in 20 ml. of pyridine is again added. The resulting solution is allowed to stand overnight then is poured into ice water and extracted with ether. The ether extracts are washed with dilute hydrochloric acid, dried and concentrated to give 11 g. of crude product. Trituration of the crude product with ether and recrystallization from ethyl acetateheptane gives 8.1 g. of product (A) with m.p. 157°–159°.

Analysis for: $C_{27}H_{29}NO_5S_2$: Calculated: C, 63.39; H, 5.71; N, 2.74. Found: C, 63.33; H, 5.82; N, 2.43.

A mixture of the ditosylate (A) (4.0 g.), lithium aluminum hydride (1.5 g.) and tetrahydrofuran is allowed to stir at room temperature for 1 hour under nitrogen then is refluxed overnight. Four ml. of water is added and the mixture is filtered. The collected solid is treated with dilute hydrochloric acid and extracted with ether. The ether extracts are combined with the filtrate of above and concentrated to give an oily solid (3.4 g.). Crystallization of the solid from ethanol-water gives 1.4 g. of product (B) with m.p. 173°–175°.

Analysis for: $C_{20}H_{23}NO_2S$: Calculated: C, 70.36; H, 6.79; N, 4.10. Found: C, 70.29; H, 6.65; N, 4.39.

Sodium metal (2.8 g.) is dissolved in a solution of napthalene (15.4 g.) and dimethoxyethane (130 ml.) under a nitrogen atmosphere with stirring. After 1.5 hours, product (B) (4.6 g.), in 45 ml. of dimethoxyethane, is added and the mixture is stirred for 2 hours. Water (1 ml.) is added and the mixture concentrated. The residue is dissolved in ether-water and the ether separated. The ether layer is extracted with dilute hydrochloric acid. The acid layer is basified with concentrated sodium hydroxide and extracted with ether and dried. Addition of ethereal hydrogen chloride gives 2.3 g. of the hydrogen chloride salt of the title product with m.p. 225°–227° which is collected by filtration.

Analysis for: $C_{13}H_{18}NCl \cdot \frac{1}{4} H_2O$: Calculated: C, 68.41; H, 8.16; N, 6.14. Found: C, 68.62; H, 8.10; N, 5.92.

EXAMPLE LXXX

Resolution of 5,6,7,8,9,10,11.12-Octahydro-3-Methoxy-5α-Methyl-5,11-Methanobenzocyclodecen-13β-Amine Part A A solution of racemic 5,6,7,8,9,10,11,12-octahydro-3-methoxy-5α-methyl-5,11-methanobenzocyclodecen-13β-amine (83 g.) in 200 ml. of methanol is added to a solution of d-tartaric acid (57 g.) in 500 ml. of methanol. The solution is diluted to 1 liter and allowed to stand for 2 days. Filtration gives 83.5 g. of salt with m.p. 200°–208° dec. Three recrystallizations of this salt from methanol give 21 g. of optically pure tartrate salt with m.p. 213°–215°. This is converted to optically pure base by treatment of the salt with dilute sodium hydroxide and extraction with ether. Exactly one-half of the dried ether extracts (225 ml.) are treated with 15 ml. of ethanol and acidified with ethereal hydrogen chloride. Filtration gives 5.8 g. of the hydrochloride salt of the plus rotating enantiomorph with m.p. 234°–237°.

Analysis for: $C_{17}H_{26}NOCl$ $[\alpha]_D^{25} = +46°$. Calculated: C, 69.01; H, 8.86; N, 4.73. Found: C, 68.90; H, 9.10; N, 4.42.

Part B

The mother liquors of the tartrate crystallization of above are concentrated and the residue is converted to base by treatment with dilute aqueous sodium hydroxide and extraction with ether. Removal of the ether gives 58 g. of base which is dissolved in methanol and treated with 38 g. of l-tartaric acid in methanol. The final solution has a volume of 800 ml. Filtration after 4 days of standing gives 41.3 g. of tartrate salt with m.p. 204°–209° dec. Two recrystallizations of this salt give optically pure tartrate salt with m.p. 216°–218°. Conversion to optically pure base and subquently hydrogen chloride salt as in part A yields 6.0 g. of hydrochloride salt of the minus rotating enantiomorph with m.p. 234°–237° and $[\alpha]_D^{25} = -46.0°$.

Analysis for: $C_{17}H_{26}NOCl$: Calculated C, 69.01; H, 8.86; N, 4.73. Found: C, 68.63; H, 9.10; N, 4.35.

EXAMPLE LXXXI (+)–13β-Amino-5,6,7,8,9,10,11,12-Octahydro-5α-Methyl-5,11-Methanobenzocyclodecen-3Ol The second half of the ethereal solution of optically pure plus rotating base described in EXAMPLE LXXX, Part A is concentrated to give 6.5 g. of base. This is treated with 100 ml. of 48% aqueous hydrogen bromide and heated at reflux under dry nitrogen for one-half hour then concentrated. The residual oil is crystallized from water to give 5.4 g. of hydrogen bromide salt of the title product with m.p. 268°–272° and $[\alpha]_D^{25} = +41.4°$.

Analysis for: $C_{16}H_{24}NOBr \cdot \frac{1}{4} H_2O$: Calculated: C, 58.09; H, 7.46; N, 4.23. Found: C, 58.20; H, 7.61; N, 4.23.

(−)-13β-Amino-5,6,7,8,9,10.11.12-Octahydro-5α-Methyl-5,11-Methanobenzocyclodecen-3Ol In the same manner as described for the preparation of the plus rotating isomer, from the ethereal solution of minus rotating base described in Example LXXX, Part B there is obtained 5.5 g. of hydrogen bromide salt of the title product with m.p. 269°–271° and $[\alpha]_D^{25} = -41.7°$.

Analysis for: $C_{16}H_{24}NOBr \cdot \frac{1}{4} H_2O$: Calculated: C, 58.09; H, 7.46; N, 4.23. Found: C, 58.47; H, 7.41; N, 4.26.

EXAMPLE LXXXII

13β-(Dimethylamino)-5,6,7,8,9,10,11,12-Octahydro-5α-Methyl-5,11-Methanobenzocyclodecen-3Ol A solution of 5,6,7,8,9,10,11,12-octahydro-3-methoxy-N, N, 5α-trimethyl-5,11-methanobenzocyclodecen-13β-amine, hydrochloride (5.0 g.) in 80 ml. of 48% hydrobromic acid is heated at reflux under dry nitrogen for 20 minutes then concentrated. The residue is crystallized from ethanol-ether to give 4.4 g. of the hydrobromide salt of the title product m.p. 243°–245°.

Analysis for: $C_{18}H_{28}NOBr$: Calculated: C, 61.01; H, 7.96; N, 3.95. Found: C, 61.06; H, 8.10; N, 3.85.

EXAMPLE LXXXIII 5,6,7,8,9,10,11,12-Octahydro-3-Methoxy-N,N,5α-Trimethyl-5,11-Methanobenzocyclodecen-13β-Amine N-Oxide To a cold (0°) solution of 5,6,7,8,9,10,11,12-octahydro-3-methoxy-N,N,5α-trimethyl-5,11-methanobenzocyclodecen-13β-amine (1.5 g.) in 20 ml. of dry tetrahydrofuran is added 1.0 g. of meta chloroperbenzoic acid in 10 ml. of tetrahydrofuran. The solution is stirred at 0° to 10° for 30 minutes. Two ml. of a saturated solution of hydrogen chloride in ethanol is added. After crystallization occurs, 30 ml. of ether is added and the mixture is filtered to give 1.7 g. of the hydrogen chloride salt of the title product with m.p. 170°–173° dec.

Analysis for: $C_{19}H_{30}NO_2Cl$: Calculated: C, 67.13; H, 8.90; N, 4.13. Found: C, 66.61; H, 9.04; N, 3.98.

EXAMPLE LXXXIV 6,7,8,9-Tetrahydro-N,5-Dimethyl-5,9-Methano-5H-Benzocyclohepten-10-Amine In a manner analogous to that described in Example XXXVII for the preparation of 6,7,8,9,10,11-hexahydro-3-methoxy-N,5α-dimethyl-5,10-methano-5H-benzocyclononen-12α-amine from 1.1 g. of 6,7,8,9-tetrahydro-5-methyl-5,9-methano-5H-benzocyclohepten-10-amine there is obtained 0.90 g. of the hydrogen chloride salt of the title product with m.p. 289°–290°.

Analysis for: $C_{14}H_{20}NCl$: Calculated: C, 70.72; H, 8.48; N, 5.89. Found: C, 70.40; H, 8.59; N, 5.93.

EXAMPLE LXXXV

1-(4-Bromobutyl)-1-Ethoxycarbonyl-2-Indanone

In a manner analogous to that described in Example LXXV for the preparation of 1-(3-bromopropyl)-1-ethoxycarbonyl-2-indanone, from 51 g of 1-ethoxy-carbonyl-2-indanone there is obtained 41 g. of the title product with b.p. 170 at 0.4 mm.

EXAMPLE LXXXVI

1-Ethoxycarbonyl-1,3-Butano-2-Indanone

In a manner analogous to that described in Example LXXVI for the preparation of 1-ethoxycarbonyl-1,3-propano-2-indanone, from 45 g. of 1-(4-bromo)-1-ethoxycarbonyl-2-indanone there is obtained 14.5 g. of the title product with b.p. 140° at 0.4 mm.

EXAMPLE LXXXVII

1-Ethoxycarbonyl-1,3-Butano-2-Indanone, Oxime

In a manner analogous to that described in Example LXXVII for the preparation of 1-ethoxycarbonyl-1,3-propano-2-indanone, oxime, from 11 g. of 1-ethoxycarbonyl-1,3-butano-2-indanone there is obtained 5.5 g. of the title product with m.p. 122°–4°.

EXAMPLE LXXXVIII

11-Amino-5,6,7,8,10-5,10-Methano-Benzocyclooctene-5-Methanol

In a manner analogous to that described in Example LXXXVII for the preparation of 10-amino-6,7,8,9-tetrahydro-5,9-methano-5H-benzocycloheptene-5-methanol, from 6.6 g. of 1-ethoxycarbonyl-1,3-butano-2-indanone, oxime there is obtained 4.1 g. of the title product as the hydrogen chloride salt with m.p. 197°–200°.

Analysis for: $C_{14}H_{20}NOCl$; Calculated: C, 66.26; H, 7.94; N, 5.52. Found: C, 66.40; H, 8.13; N, 5.80.

EXAMPLE LXXXIX

5,6,7,8,9,10-Hexahydro-11-Methylamino-5,10-Methanobenzocyclooctene-5-Methanol In a manner analogous to that described in Example XXXVII for the preparation of 6,7,8,9,10,11-hexahydro-3-methoxy-N,5α-dimethyl-5,10-methano-5H-benzocyclononen-12α-amine, from 3.0 g. of 11-amino-5,6,7,8,10-5,10-methano-benzocyclooctene-5-methanol there is obtained 1.9 g. of the title product as the hydrogen chloride salt with m.p. 275°–276°.

Analysis for: $C_{15}H_{22}NOCl$: Calculated: C, 67.27; H, 8.28; N, 5.23. Found: C, 67.38; H, 8.46; N, 5.19.

EXAMPLE XC

11-Dimethylamino-5,6,7,8,9,10-Hexahydro-5,10-Methanobenzocyclooctene-5-Methanol In a manner analogous to that described in Example LXIV for the preparation of 5,6,7,8,9,10-hexahydro-3-methoxy-N-5α-dimethyl-5,9-methanobenzocyclooctene-11β-amine, from 1.3 g. of 5,6,7,8,9,10-hexahydro-11-methylamino-5,10-methanobenzocyclooctene-5-methanol 1.25 g. of the title product as the hydrogen chloride salt, m.p. 243°–4°.

Analysis for: $C_{16}H_{24}NOCl$: Calculated: C, 68.19; H, 8.58; N, 4.97. Found: C, 67.97; H, 8.67; N, 4.50.

EXAMPLE XCI

To prepare: 1-(5-bromopentyl)-6,7-dimethoxy-1-methyl-2-tetralone react 6,7-dimethoxy-1-methyl-2-tetralone with 1,5-dibromopentane as taught in Example I.

To prepare: 1-allyl-1(4-chlorobutyl)-7-methoxy-2-tetralone react 1-allyl-7-methoxy-2-tetralone with 1-bromo-4-chlorobutane as taught in Example I.

To prepare: 7-fluoro-1-(5-bromopentyl)-1-methyl-2-tetralone react 7-fluoro-1-methyl-2-tetralone with 1,5-dibromopentane as taught in Example I.

EXAMPLE XCII

To prepare: 5,6,7,8,9,10,11,12-octahydro-2,3-dimethoxy-5-methyl-5,11-methanobenzocyclodecen-13-one treat 1-(5-bromopentyl)-6,7-dimethoxy-1-methyl-2-tetralone with sodium hydride as taught in Example X.

To prepare: 5-allyl-6,7,8,9,10,11-hexahydro-3-methoxy-5,10-methano-5H-benzocyclononen-12-one treat 1-allyl-1-(4-chlorobutyl)-7-methoxy-2-tetralone with sodium hydride as taught in Example X.

To prepare: 3-fluoro-5,6,7,8,9,10,11,12-octahydro-5-methyl-5,11-methanobenzocyclodecen-13-one treat 7-fluoro-1-(5-bromopentyl)-1-methyl-2-tetralone with sodium hydride as taught in Example X.

EXAMPLE XCII

To prepare: 5,6,7,8,9,10,11,12-octahydro-2,3-dimethoxy-5-methyl-5,11-methanobenzocyclodecen-13-one, oxime treat 5,6,7,8,9,10,11,12-octahydro-2,3-dimethoxy-5-methyl-5,11-methanobenzocyclodecen-13-one with hydroxyl amine hydrochloride as taught in Example XIX, method C.

To prepare: 5-allyl-6,7,8,9,10,11-hexahydro-3-methoxy-5,10-methano-5H-benzocyclononen-12-one, oxime treat 5-allyl-6,7,8,9,10,11-hexahydro-3-methoxy-5,10-methano-5H-benzocyclononen-12-one with hydroxyl amine hydrochloride as taught in Example XIX, method C.

To prepare: 3-fluoro-5,6,7,8,9,10,11,12-octahydro-5-methyl-5,11-methanobenzocyclodecen-13-one, oxime treat 3-fluoro-5,6,7,8,9,10,11,12-octahydro-5-methyl-5,11-methanobenzocyclodecen-13-one with hydroxyl amine hydrochloride as taught in Example XIX, method C.

EXAMPLE XCIV

5,6,7,8,9,10,11,12-Octahydro-2,3-Dimethoxy-5-Methyl-5,11-Methano-Benzocyclodecen-13-Amine Using a procedure analogous to that described in Example XXVIIA for the preparation of 6,7,8,9,10,11-hexahydro-3-methoxy-5-methyl-5,10-methano-5H-benzocyclononen-12-amine from 5.2 g. of 5,6,7,8,9,10,11,12-octahydro-2,3-dimethoxy-5-methyl-5,11-methano-benzocyclodecen-13-one, oxime there is obtained 4.17 g. of the title product which is converted to the hydrogen chloride addition salt m.p. 281°–283°.

Analysis for: $C_{18}H_{28}O_2NCl$: Calculated: C, 66.40; H, 8.67; N, 4.30. Found: C, 66.27; H, 8.81; N, 4.23.

EXAMPLE XCV

5-Allyl-6,7,8,9,10,11-Hexahydro-3-Methoxy-5,10-Methano-5-H-Benzocyclononen-12-Amine Using a procedure analogous to that described in Example XXVIIA for the preparation of 6,7,8,9,10,11-hexahydro-3-methoxy-5-methyl-5,10-methano-5H-benzocyclononen-12-amine, from 13.3 g. of 5-allyl-6,7,8,9,10,11-hexahydro-3-methoxy-5,10-methano-5H-benzocyclononen-12-one, oxime there is obtained 6.3 g. of the title product whih is converted to the fumaric acid addition salt m.p. 219°–220°.

Analysis for: $C_{19}H_{29}NO_5$: Calculated: C, 68.19; H, 7.54; N, 3.62. Found: C, 68.42; H, 7.78; N, 3.99.

EXAMPLE XCVI

3-Fluoro-5,6,7,8,9,10,11,12-Octahydro-5α-Methyl-5,11-Methanobenzocyclodecen-13β-Amine Using a procedure analogous to that described in Example XXVIIA for the preparation of 6,7,8,9,10,11-hexahydro-3-methoxy-5-methyl-5,10-methano-5H-benzocyclononen-12-amine, from 14.1 g. of 3-fluoro-5,6,7,8,9,10,11,12-octahydro-5-methyl-5,11-methanobenzocyclodecen-13-one, oxime there is obtained 10.5 g. of the title product which is converted to the fumaric acid addition salt (8 g.) of the title product m.p. 218°–220°.

Analysis for: $C_{20}H_{20}FNO_4$: Calculated: C, 66.10; H, 7.21; N, 3.85. Found: C, 65.80; H, 7.26; N, 3.58.

EXAMPLE XCVII

3-Methoxy-5α-Methyl-5,6,7,8,9,10,11,12-Octahydro-5,11-Methanobenzocyclodecen-13α-Amine From the mother liquors remaining after the isolation of the product of Example XXXV, 3-methoxy-5α-methyl-5,6,7,8,9,10,11,12-octahydro-5,11-methanobenzocyclodecen-13β-amine, there is obtained by following a procedure analogous to that described in Example XXXIV part C for the isolation of 5,6,7,8,9,10-hexahydro-3-methoxy-5α-methyl-5,9-methano-benzocycloocten-11β-amine, hydrochloride, the title product, m.p. 207°–208°.

EXAMPLE XCVIII

3-Methoxy-N-5α-Dimethyl-5,6,7,8,9,10,11,12-Octahydro-5,11-Methanobenzocyclodecen-13α-Amine In a manner analogous to that described in Example XXXVII for the preparation of 6,7,8,9,10,11-hexahydro-3-methoxy-N,5α-dimethyl-5,10-methano-5H-benzocyclononen-12α-amine there is obtained from 3-methoxy-5α-methyl-5,6,7,8,9,10,11,12-octahydro-5,11-methanobenzocyclodecen-13α-amine the title product with an NMR Analysis having an N-CH₃ signal at $\delta = 2.48$ ppm. (free base).

EXAMPLE XCIX

(−)-13β-Amino-5,6,7,8,9,10,11,12-Octahydro-5α-Methyl-5,11-Methanobenzocyclodecen-3-Ol, Cyclopropanecarboxylate Hydrochloride A mixture of 5.0 g. of (−)-13β-amino-5,6,7,8,9,10,11,12-octahydro-5α-methyl-5,11-methanobenzocyclodecen-3-ol, hydrobromide, 2.8 g. of carbobenzyloxychloride, 200 ml. of methylene chloride and 200 ml. of a saturated aqueous sodium bicarbonate solution is stirred at room temperature for 2 hours. The methylene chloride layer is separated, dried and concentrated to give an oil which is washed 4 times with hexane. The resultant viscous oil is dissolved in 200 ml. of benzene and to this stirred solution is added 1.7 g. of trimethylamine followed by 1.7 g. of cyclopropane carbonyl chloride in a little benzene. After one-half hour of stirring the mixture is extracted with water, washed with sodium bicarbonate, dried and concentrated to give a viscous glass. This glassy material is dissolved in 250 ml. of tetrahydrofuran containing 3.0 g. of dry hydrogen chloride. This solution is hydrogenated over 1.6 g. of 10% palladium on carbon at 45 psi. hydrogen pressure for 3 hours. The catalyst is filtered and the filtrate is concentrated to give a viscous glass. The glassy material is crystallized from tetrahydrofuran-ether to give 2.3 g. of white crystals with m.p. 276°–277° dec. An additional 0.62 g. is obtained from the mother liquors on further addition of ether and standing. The analytical sample had m.p. 278° dec., $[\alpha]_D^{25} = -39.5°$.

Analysis for: $C_{20}H_{28}NO_2Cl_2$: Calculated: C, 68.65; H, 8.07; N, 4.00. Found: C, 68.26; H, 7.95; N, 3.95.

The subject matter which the applicants regard as their invention is particularly pointed out and distinctly claimed as follows:

1. A compound of the formula:

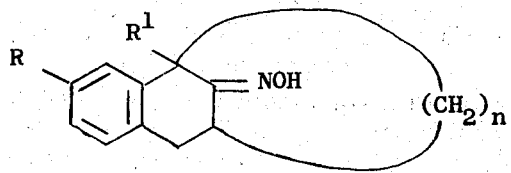

wherein R is hydrogen, lower alkyl, lower alkyloxy, hydroxy, phen(lower)alkyloxy, halogen, trifluoromethyl, or

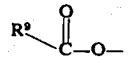

wherein $R^9$ is lower alkyl of 1 to 6 carbon atoms either straight, branched chain, or concatenated to form a carbocyclic ring, or a carbocyclic aromatic nucleus of 6 to 10 carbon atoms, or a lower alkyl substituted carbocyclic aromatic nucleus of 6 to 10 carbon atoms; $R^1$ is lower alkyl, lower alkenyl, or phen(lower)alkyl; and $n$ is an integer from 4 to 5.

2. A compound as defined in claim 1 wherein $n$ is 4.
3. A compound as defined in claim 2 which is 6,7,8,9,10,11-hexahydro-3-methoxy-5-methyl-5,10-methano-5H-benzocyclononen-12-one, oxime.
4. A compound as defined in claim 2 which is 5-ethyl-6,7,8,9,10,11-hexahydro-3-methoxy-5,10-methano-5H-benzocyclononen-12-one, oxime.
5. A compound as defined in claim 1 wherein $n$ is 5.
6. A compound as defined in claim 5 which is 3-fluoro-5,6,7,8,9,10,11,12-octahydro-5-methyl-5,11-methano-benzocyclodecen-13-one, oxime.
7. A compound as defined in claim 5 which is 5-methyl-5,6,7,8,9,10,11,12-octahydro-5,11-methanobenzocyclodecen-13-one, oxime.
8. A compound as defined in claim 5 which is 5-methyl-3-methoxy-5,6,7,8,9,10,11,12-octahydro-5,11-methanobenzocyclodecen-13-one, oxime.

* * * * *